United States Patent [19]

Buxbaum et al.

[11] Patent Number: 5,385,915
[45] Date of Patent: Jan. 31, 1995

[54] TREATMENT OF AMYLOIDOSIS ASSOCIATED WITH ALZHEIMER DISEASE USING MODULATORS OF PROTEIN PHOSPHORYLATION

[75] Inventors: Joseph D. Buxbaum, Flushing; Samuel E. Gandy; Paul Greengard, both of New York, all of N.Y.

[73] Assignee: The Rockefeller University, New York, N.Y.

[21] Appl. No.: 73,112

[22] Filed: Jun. 7, 1993

Related U.S. Application Data

[63] Continuation-in-part of Ser. No. 809,174, Dec. 17, 1991, Pat. No. 5,242,932, and a continuation-in-part of Ser. No. 524,202, May 16, 1990, abandoned.

[51] Int. Cl.⁶ ............... A01N 43/16; A01N 43/42; A61K 31/47
[52] U.S. Cl. .................. 514/313; 514/453; 514/468; 514/510; 514/691; 514/729; 514/739; 514/766
[58] Field of Search ............... 514/313, 453, 468, 510, 514/691, 729, 739, 766

[56] References Cited

U.S. PATENT DOCUMENTS 5,242,932 9/1993 Gandy et al. .................. 514/313

OTHER PUBLICATIONS

J. L. Biedler et al., "Morphology and Growth, Tumorigenicity, and Cytogenetics of Human Neuroblastoma Cells in Continuous Culture", *Cancer Res.*, 33, pp. 2643–2652.

Buxbaum et al., "Processing of Alzheimer β/A4 amyloid precursor protein: Modulation by agents that regulate protein phosyphorylation" *Proc. Natl. Acad. Sci. U.S.A.*, 87, pp. 6003–6006 (1990).

Caporaso et al., "Chloroquine Inhibits Intracellular Degradation But Not Secretion of Alzheimer β/A4 Amyloid Precursor Protein", *Proc. Natl. Acad. Sci. U.S.A.*, 87, pp. 2252–2256 (Mar. 15, 1992).

Cole et al., "Evidence for Lysosomal Processing of Amyloid β-Protein Precursor in Cultured Cells", *Neurochem. Res.*, 14, pp. 933–939 (1989).

Crandall et al., "Inverse Diffusion Methods for Data Peak Separation", *Anal. Biochem.*, 167, p. 15 (1987).

Donnelly, R. J. et al., "Interleukin-1 Stimulates the Beta-Amyloid Precursor Protein Promoter", *Cell Mol. Neurobiol.*, 10, pp. 485–495, (1990).

Glenner and Wong, "Alzheimer's Disease: Initial Report of the Purification and Characterization of a Novel Cerebrovascular Amyloid Protein", *Biochem Biophys. Res. Commun.*, 120, pp. 885–890 (1984).

Glenner and Wong, "Alzheimer's Disease and Down's Syndrome sharing of a Unique Cerebrovascular Amyloid Fibril Protein", *Biochem Biophys. Res. Commun.*, 122, pp. 1131–1135 (1984).

Gardella, et al., "Intact Alzheimer Amyloid Precursor Protein (APP) is present in Platelet Membranes and is Encoded by Platelet mRNA", *Biochem. Biophys. Res. Commun.*, 173, pp. 1292–1298 (1990).

Goldgaber et al., "Interleukin 1 regulates syntheis of amyloid β-protein precursor mRNA in human endothelial cells", *Proc. Natl. Acad. Sci. USA.*, 86, pp. 7606–7610 (1989).

Griffin et al., "Brain interleukin 1 and S-100 immunoreactivity are elevated in Down syndrome and Alzheimer disease", *Proc. Natl. Acad. Sci. USA.*, 86, pp. 7611–7615 (1989).

(List continued on next page.)

*Primary Examiner*—Nathan M. Nutter
*Attorney, Agent, or Firm*—Klauber & Jackson

[57] ABSTRACT

A method of regulating phosphorylation of proteins involved in controlling processing or function of key proteins found in intracellular neurofibrillary tangles and extracellular amyloid plaques associated with Alzheimer disease comprising introducing an effective amount of a kinase modulator or phosphatase modulator, the modulator capable of increasing or decreasing the rate of proteolytic processing, or modulating the function, of said key proteins.

36 Claims, 12 Drawing Sheets

OTHER PUBLICATIONS

Harlow et al., Antibodies: A Laboratory Manual (Cold Spring Harbor N.Y. 1988).

Huttner et al., "Multiple phosphorylation sites in protein I and their differential regulation by cyclic AMP and calcium", *Proc. Natl. Acad. Sci. U.S.A.*, 76, pp. 5402-5406 (1979).

Kang et al., "The precursor of Alzheimer's Disease amyloid A4 protein resembles a cell-surface receptor", *Nature* (London), 325, pp. 733-736 (1987).

E. A. Jaffe, "Culture of Human Endothelial Cell Derived from Umbilical Veins", *J. Clin. Invest.*, 52, pp. 2745-2746.

La Frauci et al., "Characterization of 5'-End Region and the First Two Exons of the $\beta$-Protein Precursor Gene", *Biochem. Biophys. Res. Commun.*, 159, pp. 297-304 (1989).

Manning et al., "Identification in rodents and other species of an mRNA homologous to the human $\beta$-amyloid precursor", *Brain Res.*, 427, pp. 293-297 (1988).

Masters et al. "Amyloid plaque core protein in Alzheimer disease and Down syndrome", *Proc. Natl. Acad. Sci., U.S.A.*, 82, pp. 4245-4249 (1985).

Pang et al., "Protein tyrosine phosphorylation in synaptic vesicles", *Proc. Natl. Acad. Sci. U.S.A.*, 85, pp. 762-766 (1988).

R. Pinkas-Kramarski et al., "Growth Factor-Like Effects Mediated by Muscarinic Receptors in PC12M1 Cells", *J. Neurochem.*, 59(6), pp. 2158-2166 (1992).

Podlisny et al., "Gene Dosage of the Amyloid $\beta$ Precursor Protein in Alzheimer's Disease", *Science*, 238, pp. 669-671 (1987).

Price et al., "Cellular and Molecular Biology of Alzheimer's Disease", *Bio. Assay*, 10, pp. 69-71 (1989).

Sisodia et al., "Evidence that $\beta$-Amyloid Protein in Alzheimer's Disease Is Not Derived by Normal Processing", *Science*, 248, pp. 492-495 (1980).

R. P. Smith et al., "Platelet Coagulation Factor $XI_a$-Inhibitor, a Form of Alzheimer Amyloid Precursor Protein", *Science*, 248, pp. 1126-1128 (1990).

St. George-Hyslop et al. "The Genetic Defect Causing Familial Alzheimer's Disease Maps on Chromosome 21", *Science*, 235, pp. 885-890 (1987).

Tanzi et al, "The Amyloid $\beta$ Protein Gene Is Not Duplicated In Brains from Patients with Alzheimer's Disease", *Science*, 238, pp. 666-669 (1987).

Warren et al., "$\beta$-Amyloid Gene Is Not Present in Three Copies of Autopsy-Validated Alzheimer's Disease", *Genomic*, 1, pp. 307-312 (1987).

Weidemann et al., "Identification, Biogenesis, and Localization of Precursors of Alzheimer's Disease A4 Amyloid Protein", *Cell*, 57, pp. 115-126 (1989).

Yamada et al., "Structure and Expression of the Alternatively-Spliced Forms of mRNA for the Mouse Homolog of Alzheimer's Disease Amyloid Beta Protein Precursor", *Biochem. Biophys. Res. Commun.*, 158, pp. 906-912 (1987).

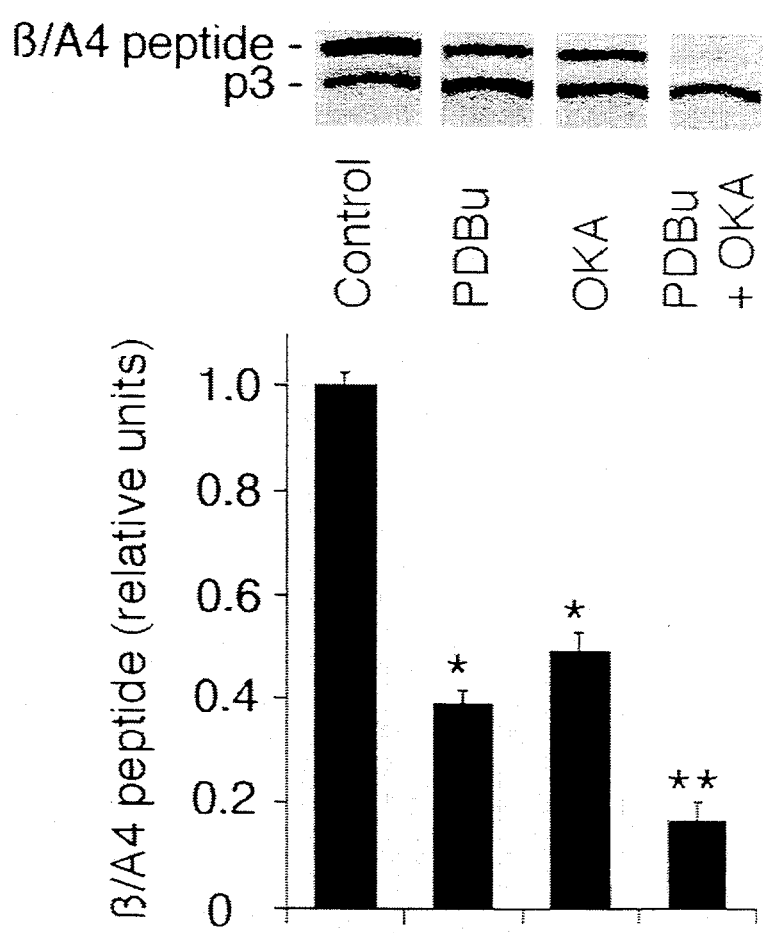
FIG. IIA

TREATMENT OF AMYLOIDOSIS ASSOCIATED WITH ALZHEIMER DISEASE USING MODULATORS OF PROTEIN PHOSPHORYLATION

CROSS-REFERENCE TO RELATED APPLICATIONS

The present application is a continuation-in-part of Copending application Ser. No. 07/809,174, filed Dec. 17, 1991 and now U.S. Pat. No. 5,242,952, and copending application Serial No. 07/524,202, filed May 16, 1990 and now abandoned. The disclosures thereof are incorporated herein by reference.

BACKGROUND OF THE INVENTION

1. Field of the Invention

The present invention concerns a method for the treatment of amyloidosis associated with Alzheimer's disease by administering to a patient an effective amount of at least one agent that modulates or affects the phosphorylation of proteins in mammalian cells.

2. Background Information

Alzheimer's disease (AD) is a brain disorder characterized by altered protein catabolism. From the work of several laboratories, altered protein phosphorylation has been implicated in the formation of the intracellular neurofibrillary tangles found in Alzheimer's disease. However, a role for protein phosphorylation in the catabolism of the amyloid precursor protein (APP), from which is derived the major component of amyloid plaques found in AD, has not been demonstrated.

Alzheimer's disease is the most common single cause of dementia in late life. Individuals with Alzheimer's disease are characterized by progressive memory impairments, loss of language and visuospatial skills and behavior deficits (McKhann et al., 1986, Neurology, 34:939–944). The cognitive impairment of individuals with Alzheimer's disease is the result of degeneration of neuronal cells located in the cerebral cortex, hippocampus, basal forebrain and other brain regions. Histologic analyses of Alzheimer's disease brains obtained at autopsy demonstrated the presence of neurofibrillary tangles (NFT) in perikarya and axons of degenerating neurons, extracellular neuritic (senile) plaques, and amyloid plaques inside and around some blood vessels of affected brain regions. Neurofibrillary tangles are abnormal filamentous structures containing fibers (about 10 nm in diameter) that are paired in a helical fashion, therefore also called paired helical filaments. Neuritic plaques are located at degenerating nerve terminals (both axonal and dendritic), and contain a core compound of amyloid protein fibers.

During the past several years, primary pathological markers associated with Alzheimer's disease have been characterized. The biochemical analyses of three forms of Alzheimer brain lesions, tangles, neuritic plaques, and cerebrovascular plaques, have revealed protein sequence information, and have facilitated subsequent cDNA cloning and chromosomal mapping of some of the corresponding genes. Immunological studies have identified several candidates for protein constituents of the paired helical filaments (PHF), including microtubule-associated protein 2 (MAP-2), tau, and ubiquitin.

A central feature of the pathology of Alzheimer's disease is the deposition of amyloid protein within plaques. The 4 kDa amyloid protein (also referred to as A4, APC, $\beta$-amyloid or B/A$_4$ peptide), is a truncated form of the larger amyloid precursor protein (APP) which is encoded by a gene localized on chromosome 21. Genetic analysis has revealed that the APP gene does cosegregate with familial Alzheimer's disease in certain families.

Initial studies of individuals with Down's syndrome (DS), caused by trisomy of chromosome 21, indicate that these individuals develop Alzheimer-like pathology beyond the second decade of life.

Age, genetic elements, and, possibly environmental factors appear to contribute to cellular pathology of Alzheimer's disease. A fundamental but unanswered question in the pathogenesis of Alzheimer's disease is the relationship between abnormalities of neurons and the deposition of amyloid. Specifically, the cellular origin of pathological events leading to the deposition of amyloid fibrils adjacent to some areas of the blood-brain barrier (cerebrovascular amyloid) and in the proximity of nerve terminals (neuritic plaques) in specific brain regions as well as extracellular amyloid in plaques cores is not known. Glenner and Wong have described the purification and characterization of meningeal amyloid from brains of both individuals with Alzheimer's disease (Glenner and Wong, 1984, Biochem. Biophys. Res. Commun., 120:885–890) or Down's Syndrome (Glenner and Wong, 1984, Biochem. Biophys, Res. Commun., 122:1131–1135) and determined the N-terminal peptide sequences. Among 24 residues analyzed, the two amyloid peptides showed only one difference, namely at amino acid position 11 (glutamine in Alzheimer's disease amyloid versus glutamic acid in Down's Syndrome amyloid) among 24 residues analyzed. Subsequent studies of amyloid from Alzheimer brain plaque cores revealed amino acid sequences identical to the reported Down's Syndrome cerebrovascular amyloid data (Masters et al, 1985, Proc. Natl. Acad. Sci. U.S.A., 82:4245–4249). cDNA analysis of APP transcripts from both normal tissue and Alzheimer brain material demonstrated the presence of the codon for glutamic acid at this position.

The availability of protein sequence information from the amyloid protein in Alzheimer brains enable the design of synthetic oligonucleotides complementary to the putative messenger RNA transcripts. Four groups have independently reported successful cloning of cDNAs including the region of the amyloid protein sequence. One group cloned the apparent full-length transcript (approximately 3.4 kb) for APP from a human fetal brain CDNA library. The 695-residue amyloid precursor protein (APP$_{695}$) shows typical features of a glycosylated cell-surface transmembrane protein. The C-terminal 12 to 14 residues of the A4 protein reside in the putative transmembrane domain of the precursor and 28 N-terminal residues are in the "extracellular domain". Genomic mapping localized the APP gene on human chromosome 21 using human-rodent somatic cell hybrids. Applying in situ hybridization techniques, this gene was sublocalized to chromosome 21q21 and more recently at the border of 21q21-22.

Chromosome 21 has been the subject of intensive studies because of its involvement in Down's Syndrome (trisomy 21). While 95% of individuals with Down's Syndrome are trisomic for the entire chromosome 21, 2–3% are mosaics, i.e., trisomic in only some cells, and 3–4% are caused by triplication (translocation) of the distal part of the long arm (21q22) of chromosome 21.

The occurrence of such translocation has led to the conclusion that Down's Syndrome can be attributed to trisomy of the distal part. (the "pathological region") of chromosome 21. To date, it is not known precisely where the breakpoint on the q arm of chromosome 21 is located, and it is not known whether individuals with Down's Syndrome, who have partial trisomy, develop Alzheimer pathology. In this context, it will be of particular interest to determine if the APP gene maps within the "pathological region" of chromosome 21. The localization of the APP gene on the long arm of chromosome 21, together with the apparent development of Alzheimer's disease pathology in individuals with Down's Syndrome, provides a potential mechanism for the formation of amyloid on the basis of overexpression of a number of genes on chromosome 21, including the APP gene. Initial studies of genomic DNA from sporadic (nonfamilial) Alzheimer's disease cases and "karyotypically normal" individuals with Down's Syndrome have implicated the presence of microduplication of a segment of chromosome 21 including the APP gene. However, subsequent analyses of large numbers of individuals with Alzheimer's disease by several laboratories has not confirmed these findings (Tanzi et al., 1987, *Science*, 238:666–669; St. George-Hyslop et al., 1987, *Science*, 238:664–666; Podlisny et al., 1987, *Science*, 238:669–671; Warren et al., 1987, *Genomics*, 1:307-3 12).

Chromosomal mapping experiments, using human APP probes in human/rodent cell hybrids, have shown cross-hybridization with mouse and hamster genomic DNA. Southern blot analysis of DNA from various species has indicated that the APP gene is highly conserved during evolution. Comparison of the mouse APP sequence with the sequence from rat shows 99% homology on the protein level; furthermore, the human sequence is 96.8% homologous to the mouse sequence and 97.3% homologous to the rat sequence. Based on the striking conservation of APP protein, Yamada et al. (1987, *Biochem. Biophys. Res. Commun.* 158:906–912) have calculated the evolutionary rate of changes at the amino acid level to be $0.1 \times 10^{-9}$/site/year, which is comparable to that of cytochrome C. Recently, K. White and colleagues have cloned a *Drosophila* gene which is highly homologous to large regions of the APP sequence. Northern blot experiments have confirmed these data at the level of mRNA and have demonstrated for various mammalian species the ubiquitous expression of APP transcripts in a number of different tissues (Manning et al., 1988, *Brain Res.*, 427:293–297).

Kang et al. (Nature 325:733–736) reported the presence of two distinct bands ($-3.2$ kb and $-3.4$ kb) by Northern analysis of human fetal brain mRNA using APP cDNA as a probe. This finding suggests either differential splicing of mRNA or alternative usage of polyadenylation sites. Both posttranscriptional events were found to be operative following detailed investigation by several groups. First, Kang et al., supra, indicated a potential polyadenylation signal (AATAAA tandem repeat) 259 bp upstream of the 3' end of the reported APP full-length APP cDNA. The analysis of eight other full-length APP cDNA clones obtained from a human fetal brain cDNA library demonstrated in a 1:1 ratio between shorter cDNAs ($-3.2$ kb) using the first polyadenylation signal versus the original cDNA forms ($-3.4$ kb) using the second polyadenylation signal. Interestingly, all eight clones encoded for 695 residues of APP. The alternative use of different polyadenylation signals in APP transcripts was confirmed by other laboratories. A number of groups have screened several tumor cell-line derived cDNA libraries for the presence of APP transcripts and identified clones encoding new APP molecules containing an additional domain. This domain possesses striking homology to the Kunitz family of serine protease inhibitors. In particular, these cDNA sequences contain an additional 167 bp insert at residue 289 of the APP-695 precursor which encodes a 56 amino acid sequence of high sequence of homology to aprotinin, a well-characterized inhibitor of "trypsin-like" serine proteases. The peptide sequences flanking this region of insert are identical to the original $APP_{695}$, clone resulting in an open reading frame of 751 residues ($APP_{751}$). A third APP form has been isolated with another addition of a 19 amino acid domain at the C-terminal end of the 56 amino acid "aprotinin-like" region of $APP_{751}$, thus resulting in a larger protein of 770 residues ($APP_{770}$). Transient expression of $APP_{770}$ in COS-1 cells conferred a marked inhibition of trypsin activity in cell lysates. Both additional domains have been found to be encoded by discrete exons and all three transcripts ($APP_{695}$, $APP_{751}$, $APP_{770}$) are generated by differential splicing of a single gene on chromosome 21. These protease inhibitor domains have also recently been found to be present in mouse and rat species.

The relationship between the three different amyloid precursor forms and the formation of amyloid in Alzheimer's disease is not known. In particular, it is not known whether a specific form of APP contributes to A4 deposition. It is possible that either an imbalance in the relative expression levels of the three APP forms or their over-expression might be involved in Alzheimer's disease pathology. Initial in situ hybridization analyses using APP cDNA probes in human CNS sections indicated that many neuronal cell types express these mRNAs, but because of the nature of the probes used, these studies did not allow a differential analysis of the various APP transcripts. Furthermore, there is little documented correlation between APP mRNA levels, amyloid deposition and neuronal degeneration in Alzheimer's disease. However, it appears that high levels of APP mRNAs alone do not form a sufficient prerequisite or cellular pathology in either the aging or Alzheimer's disease brain (Higgins et al., supra). Specific probes which discriminate between the APP transcripts have been used for Northern analysis and the results suggest a developmental and tissue-specific pattern of expression of these mRNAs.

Recently, 5'-end cDNA probes from full-length APP cDNA clones have been used to isolate genomic clones containing the 5'-end of the APP gene, also referred to as precursor of Alzheimer's Disease A4 amyloid protein (PAD) gene (1988, *EMBO J.*, 1:2807–2813; La Fauci et al, 1989, *Biochem. Biophys. Res. Commun.*, 159:297–304). Approximately 3.7 kb of sequences upstream of the strongest RNA start site have been analyzed by Salbaum et al, 1988, supra. By a combination of primer extension and S1 protection analyses, five putative transcription initiation sites have been determined within a 10 bp region. This $-3.7$ kb region lacks a typical TATA box and displays a 72% GC-rich content in a region ($-1$ to $-400$) that confers promoter activity to a reporter gene in an in vivo assay system The absence of a typical TATA and CAAT box and the presence of multiple RNA start sites is suggestive of its function as a housekeeping gene but does not imply constitutive gene expression. The regulatory region contained within 400 bp upstream of the strongest RNA start site shows a variety of typical promoter-binding elements, including two AP-1 consensus sites, a single heat shock recognition consensus element, and several copies of a 9 bp-long GC-rich consensus sequence where sequence- specific binding has been shown to occur by gel-retardation studies. In addition, the CpG:GpC ratio in this promoter region has been found to be 1:1 in contrast to a 1:5 ratio found in many eukaryotic DNAs; CpG dinucleotides are known to control gene expression via DNA methylation. In addition, palindromic sequences capable of forming hairpin-like structures are found around the RNA start sites.

Recently, several groups of investigators have determined the consensus binding sequence (AT rich decamer) for a number of different homeobox proteins, which act most likely as transcription factors in specific regions during embryogenesis. As yet, target genes, which might be developmentally regulated by the homeobox proteins have not been identified. Such genes, however, will have an important role during embryogenesis and potentially throughout the entire lifespan. The APP gene promoter contains at least five homeobox binding sites upstream of the kNA start sites. Preliminary experiments have shown that the homeobox protein Hox-1.3 can bind at two of these sites. Thus, the APP gene, whose expression is developmentally regulated, appears to be a candidate gene for homeobox protein regulation. It is not known whether any of these putative recognition consensus elements translate the expression of the APP gene promoter.

Despite all that is known about the APP gene, the secondary defect leading to Alzheimer's disease is not yet known. With the exception of aged primates (Price et al., Bio Assays, 1989, 10:69-74), no laboratory animal model for Alzheimer's disease exists. The introduction of genes into the germline of animals is an extremely powerful technique for the generation of disease models which will lead to a better understanding of disease mechanisms including the mechanisms of Alzheimer's disease. Cell culture and in vitro systems cannot duplicate the complex physiological interactions inherent in animal systems. Transgenic animals have been successfully generated from a number of species including mice, sheep and pig. The gene or genes of interest are microinjected directly into the pronuclei of a one-cell embryo. A high percentage of reimplanted embryos develop normally and, in a significant proportion of progeny, the transgene becomes integrated into the chromosomal DNA. Usually, multiple copies of the transgene integrate as a head-to-tail array. Although mosaic animals can be generated, germline transmission of the transgene usually occurs.

In summary, Alzheimer's disease is characterized by certain neuropathological features including intracellular neurofibrillary tangles, primarily composed of cytoskeletal proteins, and extracellular parenchymal and cerebrovascular amyloid.

SUMMARY OF THE INVENTION

The present invention is concerned with a method of utilizing agents that regulate protein phosphorylation, thereby affecting the metabolism of APP. Using various of the proteins found in extracellular amyloid plaques of mammalian cells as a model system, Applicants have observed that APP metabolism is regulated by agents that regulate protein phosphorylation so that alterations in protein phosphorylation will result in the modification of the deposition of $\beta/A_4$ peptide in extracellular sites characteristic of Alzheimer's disease.

The present invention thus concerns a method of regulating phosphorylation of the proteins, e.g., introducing into a patient or into a cell of a patient, an effective amount of a kinase modulator or a phosphatase modulator, the modulator capable of indirectly increasing or decreasing the rate of proteolytic processing of APP protein and thereby regulating the production of $\beta/A_4$ peptide or alter the function of proteins found in neurofibrillary tangles.

The present invention is also directed to a method of inhibiting production of Alzheimer-type amyloidosis in a mammal comprising administering to the mammal an effective amount of at least one modulator of protein kinases or phosphatases, the modulator capable of altering the proteolytic processing of APP proteins and thereby regulating the production of $\beta/A_4$ peptide.

The present invention also relates to a treatment of amyloidosis associated with Alzheimer's disease in a mammalian patient comprising administering to the patient an effective amount of at least one agent capable of modulating proteolytic processing of APP proteins by altering phosphorylation in mammalian cells. Further, this treatment can encompass the co-administration of an agent which affects the endolysomal degradation of APP.

The present invention also relates to a method for screening for agents that modulate amyloid formation comprising contacting mammalian cells with an agent suspected of being capable of modulating the phosphorylation of proteins, and detecting alterations in the degradation of APP, and the production of $\beta/A_4$ peptide.

The assay of the present invention allows for the detection of many, if not all, of the effects of phosphorylation or dephosphorylation on the processing of APP. Effects of phosphorylation or dephosphorylation on the processing of APP which could be detected by the assay of the present invention include:

1. effects due to changes in the phosphorylation of APP which alter the conformation of APP, thereby changing its susceptibility to APP proteases;
2. effects due to changes in the phosphorylation of APP which alter the subcellular localization of APP, thereby changing its availability to APP proteases;
3. effects due to changes in the phosphorylation of APP proteases which alter the conformation of APP proteases, thereby altering their affinity for APP;
4. effects due to changes in the phosphorylation of APP proteases which alter the subcellular localization of the APP proteases, thereby changing their availability to APP;
5. effects due to changes in the phosphorylation of APP binding proteins which can then either alter the conformation of APP or the subcellular localization of APP, thereby changing their susceptibility or availability to specific APP proteases; and
6. effects due to changes in the phosphorylation of APP protease binding proteins which can then either alter the conformation of the proteases or their subcellular localization, thereby modulating its activity toward APP.

The assay of the present invention can also detect changes in APP processing caused when test agents modulate, i.e., activate or inhibit protein kinases or protein phosphatases which (a) directly alter the phosphorylation of APP, APP proteases, APP binding proteins, or APP protease binding proteins; or (b) phosphorylate or dephosphorylate other kinases, phosphatases which, in turn, alter the phosphorylation of APP, APP proteases, or APP binding protein or APP protease binding protein.

The present invention also is directed to a method for screening for agents that modulate amyloid formation in a normal or transgenic whole animal comprising administering to said animal an agent suspected of being capable of modulating phosphorylation and detecting neurodegenerative changes, changes in APP processing, or changes in $\beta/A_4$ peptide production, in the brain of the animal.

DETAILED DESCRIPTION OF THE DRAWINGS

FIG. 1. Regulation of APP processing by PDBu and okadaic acid (A) Identification of APP and APP -derived peptides in PC12 cells by immunoprecipitation with anti-APP$^{645-694}$ antibodies. Autoradiographs of PAGE gels from immunoprecipitates of [$^{35}$S]methionine labeled PC12 cells are shown. In the upper panel, an autoradiograph of the higher molecular weight region of a 6–18% gradient gel is shown. In the lower panel, an autoradiograph of a longer exposure of the lower molecular weight of the gel including the 15 kDa and 19 kDa peptides is shown. Lanes: 1, Immunoprecipitate of labeled PC12 cells under control conditions at zero-time; 2–6. Immunoprecipitates of labeled PC12 cells at 45 minutes of chase with additions at zero time; 2, Control cells; 3, Cells treated with 1 μM PDBu; 4, Cells treated with 1 μM okadaic acid; 5, Cells treated with 1 μM PDBu and 1 μM okadaic acid; 6, Cells treated with 1 μM PDBu and 1 μM okadaic acid immunoprecipitated in the presence of 100 μM APP$_{645-694}$ peptide.

(B) The putative APP forms in PC12 cells are related to human APP$_{695}$ as determined by limited proteolysis. The 113/115 kDa doublet (lane 1) and the 143/149 kDa doublet. (lane 2) were excised from the gel shown in A and subjected to limited proteolysis digestion with V8 protease and compared with similarly treated in vitro transcribed and translated human APP$_{695}$ cDNA (lane 3).

Figure 2A:
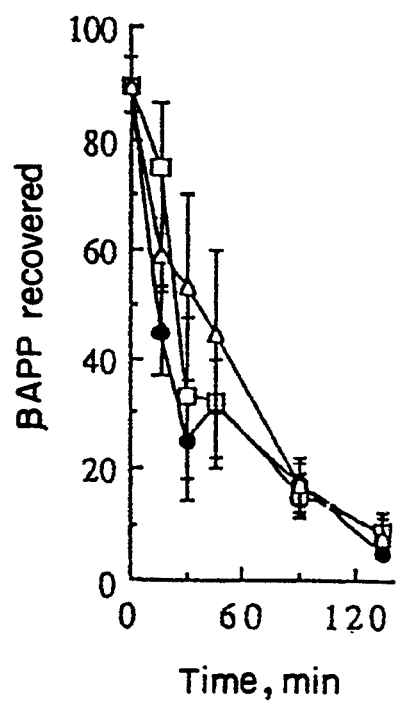
FIG. 2 are three graphs showing the effect of agents that modulate protein kinase C (PKC) activity on APP proteins in PC12 cells.
Figure 2B:
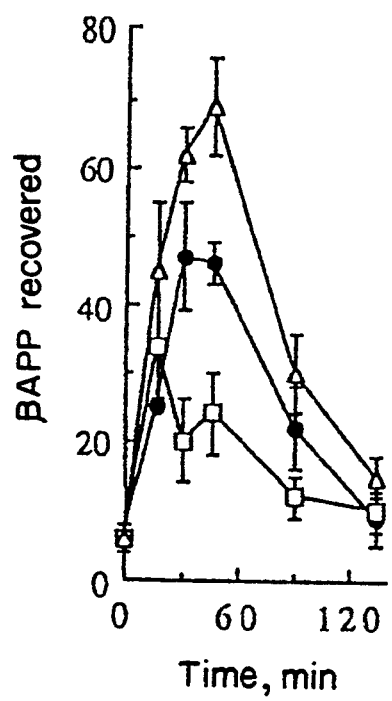
Figure 2C:
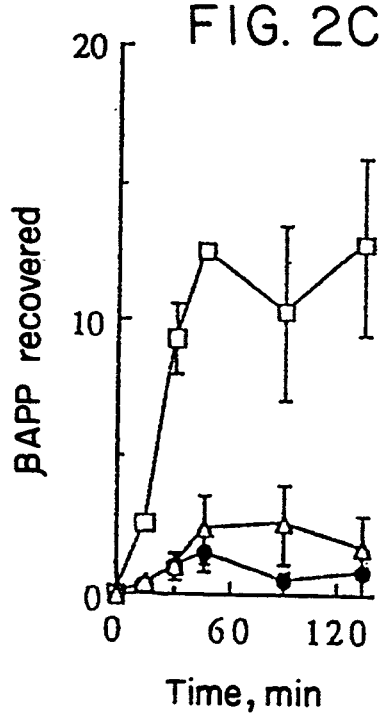

FIG. 2. Regulation of APP processing by PDBu and H-7 as a function of time

PC12 cells were metabolically labeled for 20 minutes with [$^{35}$S] methionine followed by a chase period with complete medium for the indicated times. Agents regulating PKC activity were added at the start of the chase period (zero-time). Following cell lysis, extracts were subjected to immunoprecipitation, NaDodSO$_4$-PAGE and autoradiography. The various forms of APP were quantified by scanning the autoradiogram. The results shown are the means ±SEM of four experiments. The data were normalized such that the total APP$_{751/770}$ recovered (i.e., immature and mature) at zero-time was taken as 100 units. The levels of the COOH-terminal APP fragments were insignificant at zero-time. In A and B, recovery is expressed at percent of total at zero time. In C, recovery is expressed as arbitrary units. (A) Immature APP$_{751/770}$. (B) Mature APP$_{751/770}$. (C) 15 kDa COOH-terminal fragment. Control cells (solid circles), PDBu-treated cells (open squares), H-7-treated cells (open triangles).

Figure 3A:
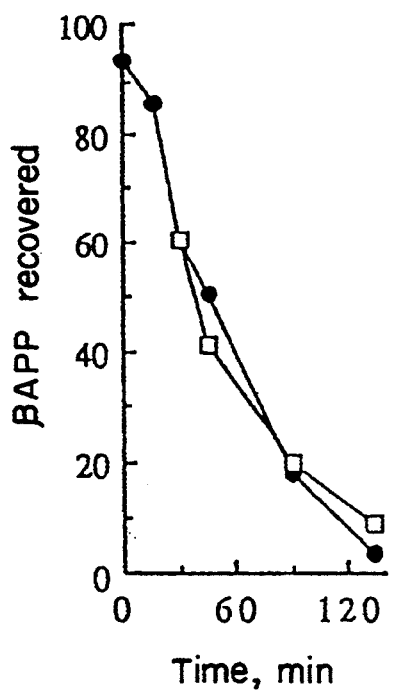
FIG. 3 are three graphs showing the effect of PDBu on APP proteins.
Figure 3B:
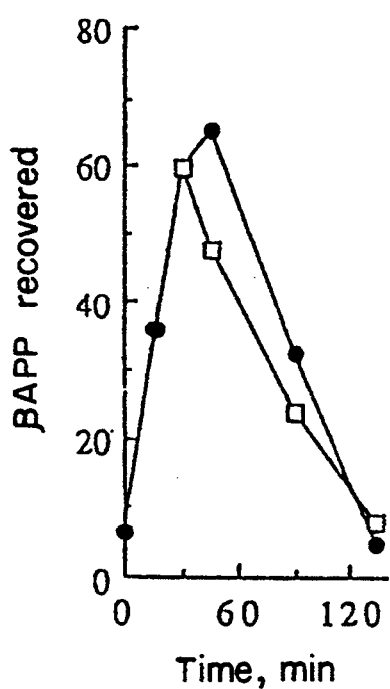
Figure 3C:
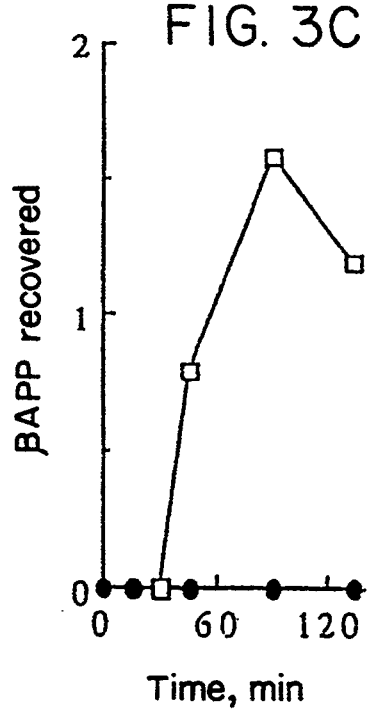

FIG. 3. Regulation by PDBU of processing of mature APP as a function of time

PDBu was added at 35 minutes of chase to allow the mature APP to approach maximal levels. All other experimental details were as described in the legend to FIG. 2. The experiment shown is representative of three separate experiments. Experimental points are the means of duplicate determination. (A) Immature APP$_{751/770}$. (B) Mature APP$_{751/770}$. (C) 15 kDa COOH-terminal fragment. Control cells (solid circles), PDBu-treated cells (open squares).

Figure 4A:
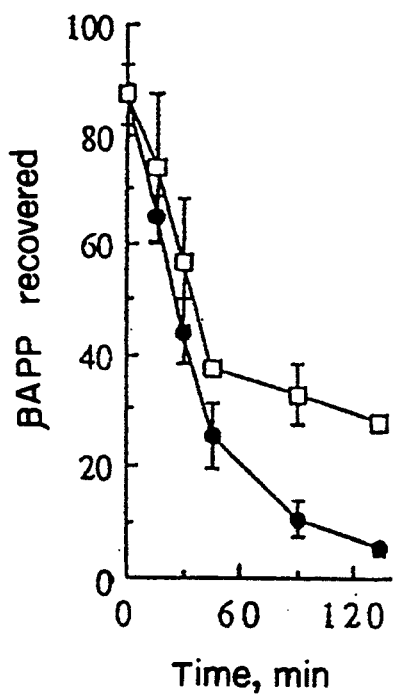
FIG. 4 are three graphs showing the regulation of APP processing by okadaic acid as a function of time.
Figure 4B:
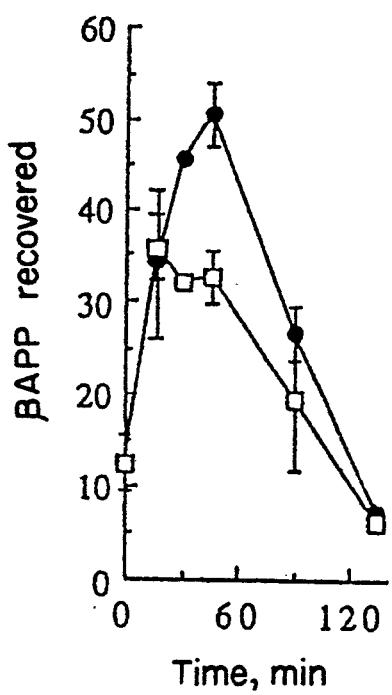

FIG. 4. Regulation of APP processing by okadaic acid as a function of time

Okadaic acid (1 μM) was added directly at the start of the chase (zero-time). All other experimental details were as described in the legend to FIG. 2. The results shown are the mean ±SEM of 4 experiments. (A) Immature APP$_{751/770}$. (B) Mature APP$_{751/770}$. (C) 15 kDa COOH-terminal fragment. Control cells (solid circles), okadaic acid treated cells (open squares).

Figure 5A:
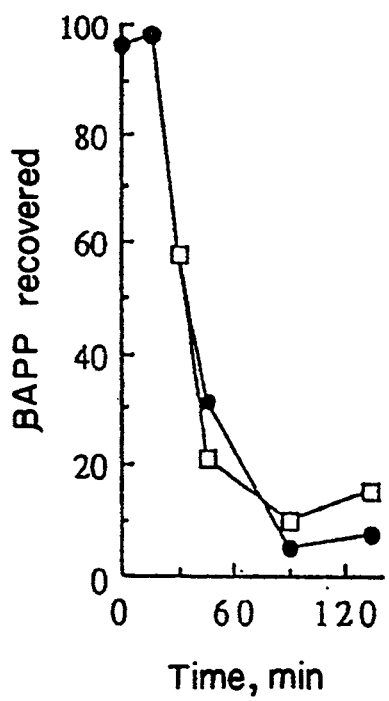
FIG. 5 are three graphs showing the regulation of APP processing by okadaic acid as a function of time.
Figure 5B:
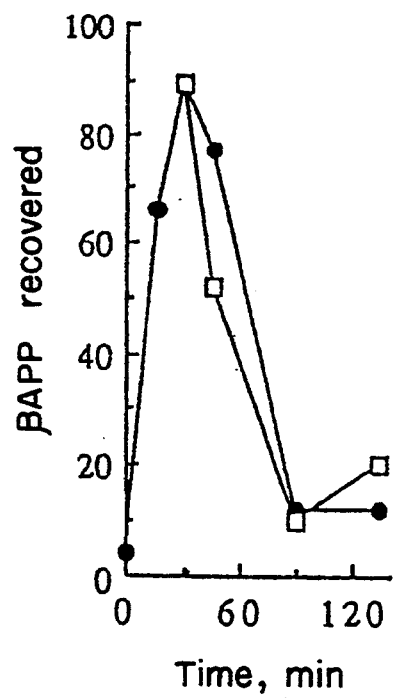

FIG. 5. Regulation by okadaic acid of processing mature APP as a function of time Okadaic acid (1 μM) was added at 35 minutes of chase to allow the mature APP to approach maximal levels. All other experimental details were as described in the legend to FIG. 2. The experiment shown is representative of two separate experiments. Experimental points are the means of duplicate determination. (A) Immature APP$_{751/770}$. (B) Mature APP$_{751/770}$. (C) 15 kDa COOH-terminal fragment. Control cells (solid circles), okadaic acid-treated cells (open squares).

FIG. 6

Recovery of mature APP in the absence (open circles) or presence (solid diamonds) of PDBu. (A) Mature APP$_{695}$. (B) Mature APP$_{751}$. (C) Mature APP$_{770}$. Results are the mean ±SEM of seven experiments (n=3 to 7 for individual time points). Statistical significance between untreated and treated samples for individual time points was determined by student's unpaired t test (*, P <0.05).

FIG. 7

Recovery of secreted amino-terminal APP fragments in the absence (open circles) or presence (solid diamonds) of PDBu. (A) Secreted $APP_{695}$. (B) Secreted $APP_{751}$. (C) Secreted $APP_{770}$. Results are the mean ±SEM of seven experiments (n=3 to 7 for individual time points). Statistical significance between untreated and treated samples for individual time points was determined by student's unpaired t test (*, P<0.05).

FIG. 8

Recovery of secreted amino-terminal APP fragments in the absence (open circles) or presence (solid diamonds) of 4α-PDBu. (A) Secreted $APP_{695}$. (B) Secreted $APP_{751}$. (C) Secreted $APP_{770}$. Results are the mean ±SEM of seven experiments (n=2 to 4 for individual time points). There was no statistical significance between untreated and treated samples for any time points was determined by student's unpaired t test (*,P<0.05).

FIG. 9

Regulation of APP secretion by various concentrations of IL-1. HUVEC were incubated for 60 minutes in the presence of the indicated concentrations of IL-1. Secreted APP was then analyzed. Within each experiment, incubations were carried out in duplicate or triplicate, and data were normalized to the maximal levels of secreted APP. The results shown represent the means ±SEM of three experiments, U, units.

FIG. 10

Regulation of APP secretion by various concentrations of IL-1ra. HUVEC were incubated for 60 minutes with 20 units of IL-1 per ml and the indicated concentrations of IL-1ra. Secreted APP was then analyzed. Within each experiment, incubations were carried out in duplicate or triplicate, and data were normalized to the levels of APP secreted in the absence of IL-1ra. The results shown represent the means ±SEM of three experiments. U, units.

FIG. 11a

Production of β/A4 peptide is regulated by protein phosphorylation. PDBu and okadaic acid treatment decreased recovery of β/A4 peptide. β/A4 peptide was immunoprecipitated from the medium of metabolically labeled CHO cells, stably expressing $APP_{695}$. Upper, Representative autoradiogram. Lower, Quantitation of β/A4 peptide. Control, no additions; PDBu, 1 μM; OKA, 2.5 μM okadaic acid. Results are the means ±SEM of 3-6 experiments performed in duplicate or triplicate. *, different from control (p<0.0001); **, different from control (p<0.0001), from PDBu alone (p<0.0005), and from OKA alone (p<0.0005).

FIG. 11b

Production of β/A4 peptide is regulated by protein phosphorylation in the presence of chloroquine. β/A4 peptide was immunoprecipitated from the medium of metabolically labeled CHO cells, stably expressing $APP_{695}$. Upper, Representative autoradiogram; Lower, Quantitation of β/A4 peptide. Control, no additions: CQ, 50 μg/ml chloroquine; PDBu, 1 μM; OKA, 2.5M okadaic acid. Results are the means ±kSEM of 3-4 experiments performed in duplicate or triplicate. *, different from control (p<0.0001); **, different from control (p<0.0001), and from chloroquine alone (p<0.05).

FIG. 12

Production of secreted APP ($APP_S$) is regulated by protein phosphorylation. $APP_S$ was immunoprecipitated from the medium of metabolically labeled CHO cells, stably expressing $APP_{695}$ upper. Representative autoradiogram. Lower, Quantitation of $APP_S$, Control, no additions; PDBu, 1 μM: OKA, 2.5 μM okadaic acid. Results are the means ±SEM of 3 experiments performed in duplicate or triplicate. *, different from control (p<0.005).

DETAILED DESCRIPTION OF THE INVENTION

Based on the observations and studies of parent applications U.S. Ser. Nos. 07/809,174 and 07/524,20.2, combined with those of the present Application, a scheme for the cellular trafficking and proteolytic processing of APP is proposed as follows:

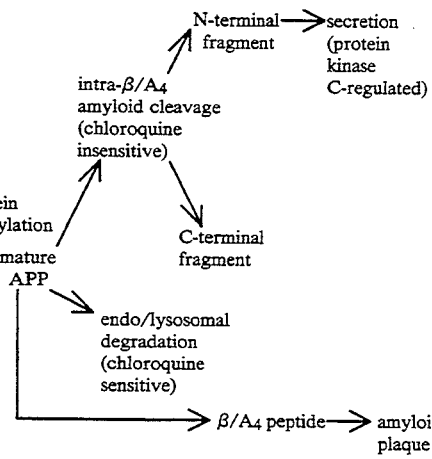

Thus, the (α-secretory) processing of APP (top route) involves cleavage of the full length molecule in the extracellular domain, near the membrane. This solubilizes the extracellular domain, which can then be recovered as a secreted protein. The alternate to this secretory pathway is degradation in the lysosome, a chloroquine-sensitive, intracellular compartment. The COOH-terminal fragment of APP remaining after secretory cleavage is also believed to be degraded in the lysosome. Stimulation of the α-secretory pathway decreases the production of β/A4 peptide by diverting APP from the pathway which produces β/A4 peptide.

The present invention utilizes various modulators of protein phosphorylation to modulate the proteolytic processing of amyloid precursor protein, thereby affecting or modulating the formation of amyloid deposits, particularly in Alzheimer's disease. Elucidation of the mechanisms of processing has lead to several therapeutic regimes which can be utilized for treatment of patients in need of such therapy.

Phorbol esters, stimulators of kinases, can decrease the rate of β/A4 peptide production since protease kinase C (PKC) targets APP for secretion. Kinase inhibitors, such as 1-(5-isoquinolinesulfonyl)-2-methylpiperazine dihydrochloride, (H7) (an inhibitor of PKC), lead to an apparent decrease in the basal rate of processing of APP, suggesting that, in the unstimulated cell, APP may be cleaved after it is phosphorylated by basally active PKC.

The following is a list of known compounds ("active compounds") which can be utilized in the present invention to affect or modulate the phosphorylation state of proteins in mammalian cells. Phosphorylation state can be modulated by inhibiting or stimulating the activity of kinases which add a phosphate moiety to proteins, or by inhibiting or stimulating phosphatases which remove a phosphate moiety from proteins.

The following is not meant to be a complete or exhaustive list, but is representative of the modulators useful in the methods of the present invention:

Kinase modulators (direct or indirect)
  Phorbol esters, e.g., phorbol-12,13-dibutyrate, phorbol. 12-myristate 13-acetate and their analogs;
  indolactam, e.g., (-)-7-octylindolactam V;
  mezerin;
  diacylglycerol;
  cAMP;
  cGMP and their analogs;
  forskolin;
  3-(N-acetylamino)-5-(N-decyl-N-methylamino)benzyl alcohol (ADMB);
  6-(N-decylamino)-4-hydroxymethylindole (DHI);
  acetylcholine;
  interleukin (IL-1);
  carbachol;
  bethanechol;
  thrombin;
  activators of adenylate and guanylate cyclase;
  activators of phospholipase C;
  compounds increasing intracellular calcium;
  staurosporine;
  auranofin;
  N-(6-aminohexyl)-1-napthalensulfonamide hydrochloride (W5);
  N-(4-aminobutyl)-2-naphthalenesulfonamide hydrochloride (W12);
  N-(6-aminohexyl)-5-chloro-1-naphthanesulfamide hydrochloride (W7);
  1-(5-isoquinolinesulfonyl)-2-methylpiperazine dihydrochloride (H7);
  N-(2-(methylamino)ethyl]-3-isoquinolinesulfonamide dihydrochloride (H8);
  N-(2-aminoethyl)-5-isoquinolinesulfonamide (H9);
  N(2-guanidinoethyl)-5-isoquinoline-sulfonamide; hydrochloride (HA1004);
  N-(-4-aminobutyl)-5-chloro-2-naphthalenesulfonamide hydrochloride (W13);
  Sphingosine;
  Tyrphostin; and
indirect kinase modulators which are agonists and antagonists of receptors for intracellular messengers known to modulate protein kinases (including the following receptors: adenosine; adrenoreceptors; angiotensin; atrial natriuretic peptide; bombesin; bradykinin; cholecystokinin and gastrin; dopamine; endothelin; GABA; glutamate; histamine; serotonin; leukotriene; muscarinic acetylcholine; neuropeptide Y; nicotinic acetylcholine; opioid; PAF; prostanoid; purinoceptors; somatostatin; tachykinin; vasopressin and oxytocin; VIP; and calcium and potassium ion channels).

Phosphatase modulators (direct or indirect)
  Okadaic acid;
  calyculin-A;
  vanadate and their analogs;
  immunosuppressives, e.g., FK506 and cyclosporin;
  compounds increasing intracellular calcium;
  mastoparan;
  acetylcholine;
  interleukin 1;
  interleukin 6;
  thrombin;
  substance P;
  interleukin-1ra; and
indirect protein phosphatase modulators which are agonists and antagonists of receptors for intercellular messengers known to modulate protein phosphatases including the following receptors: adenosine; adrenoreceptor modulators; angiotensin; bombesin; bradykinin; cholecystokinin and gastrin; dopamine; endothelin; GABA; glutamate; histamine; serotonin; leukotrienes; acetylcholine;neuropeptide Y; opiods; PAF; prostanoids; purinoceptor modulators; somatostatin; tachykinin; vasopressin and oxytocin; VIP; and calcium and potassium ion channel regulators.

It is to be understood that derivatives of the above modulators are encompassed by the present invention.

As reported (Wiedemann et al., 1989, Cell 57:115) APP in PC12 cells matures over 45 minutes. The present invention utilizes a novel assay based on PC12 cells to screen for agents that modulate amyloid formation and thus provides a novel method for screening for such agents.

Okadaic acid, as a potent inhibitor of phosphatases 1 and 2A, increases net phosphorylation for many substrates of numerous protein kinases. Therefore, the effect of okadaic acid on APP processing cannot be attributed to any one kinase and may involve phosphorylation of APP by kinases distinct from those characterized previously, or may involve phosphorylation of other proteins involved in the regulation of APP maturation and processing.

The active compounds for use in the present invention can be, and are preferably, administered as a medicament, i.e., a pharmaceutical composition.

The pharmaceutical compositions used in the methods of this invention for administration to animals and humans comprise an active compound in combination with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or, for example, a half, a third or a quarter of a daily dose will depend on whether the medicament is to be administered once, or, for example, twice three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

The therapeutic methods of the present invention also contemplate the use of more than one of the agents of the present invention which modulate the cellular trafficking and proteolytic processing of APP in differing ways. Such combinations thus may involve, for instance, an agent which affects the intra $\beta/A_4$ cleavage, e.g., a PKC stimulator, such as interleukin 1, interleukin 6, thrombin, phorbol ester, phorbol 12,13-dibutyrate, along with an agent which affects the endolysosomal degradation, e.g., chloroquine. Such agents are known from parent application U.S. Ser. No. 07/809,174. This combination has the advantages of a cumulative therapeutic effect in modulating the processing of APP, thus resulting in a reduction in the production of $\beta/A_4$ peptide production, and a concomitant reduction in amyloid formation.

The diagnostic methods of the present invention involve the screening for agents that modulate APP processing and $\beta/A_4$ peptide production, and hence amyloid formation.

Such methods may comprise administration to a normal or transgenic whole animal of an agent suspected of being capable of modulating phosphorylation of proteins and detecting neurodegenerative changes, changes in APP processing, or changes in $\beta/A_4$ peptide production in the brain of the animal, or may also comprise contacting mammalian cells with an agent suspected of being capable of modulating the phosphorylation of proteins and detecting for alterations in the metabolism of APP and $\beta/A_4$ peptide. Thus, a preferred method involves in vitro assay method for detecting changes in APP degradation comprising the steps of:
  (a) providing mammalian cells in culture;
  (b) radioactively labeling proteins produced by the mammalian cells during anabolism; then
  (c) allowing the mammalian cells to continue metabolizing in a suitable, label-free media;

(d) contacting the mammalian cells at the start of or during step (c) with an agent suspected of being capable of modulating phosphorylation that occurs during cell metabolism;

(e) lysing the mammalian cells;

(f) immunoprecipitating labeled APP or APP fragments with an antibody against APP; and (g) comparing the immunoprecipitated APP or APP fragments to standard APP or APP fragments to detect changes in APP degradation and $\beta/A_4$ peptide production.

Alternately, the method of the present invention can utilize non-radioactively labelled cells or tissue sections, and can use immunoblot deteciton of APP or APP fragments to detect changes in APP degradation and $\beta/A_4$ peptide production.

The various types of mammalian cells which can be utilized in the present invention are those such as PC12 (rat pheochromocytoma) cells, PC12 cells transfected with the $M_1$ receptor (PC12M$_1$); human umbilical vein endothelial cells (HUVEC); human glioma cells (Hs 683); human neuroblastoma cells (SH SY54); cultured cells such as neurons and glia; and brain slices.

EXAMPLES

Example 1

Phorbol 12,13-dibutyrate (PDBu), 4-α-phorbol 12,13-dibutyrate (4ePDBu) and phorbol 12-myristate 13-acetate (PMA) were purchased from LC Service Corp., Woburn, Mass. Okadaic acid was purchased from Moana BioProducts, Inc., Honolulu, Hi. 1-(5-isoquinolinesulfonyl)-2-methylpiperazine dihydrochloride (H7) was purchased from Seikagada Kogyo Co., Japan.

A synthetic peptide corresponding to the cytoplasmic domain of APP (APP$_{645-694}$, the numbering of amino acids corresponds to those of human APP$_{695}$,) was prepared by the Yale Protein and Nucleic Acid Chemistry Facility (New Haven, Conn.). Antibodies were prepared by immunizing rabbits with this synthetic peptide corresponding to APP$_{645-695}$. Immunoprecipitation was performed as described in Pang et al., 1988, *Proc. Natl. Acad. Sci. U.S.A.*, 85:762-766. Sera bearing high efficiency (>90%) immunoprecipitating activity for recombinant APP were affinity purified on columns of Sepharose-APP$_{645-695}$ as described in Harlow et al., *Antibodies: A Laboratory Manual* (Cold Spring Harbor, N.Y. 1988). The antisera used here recognized three proteins of $M_r$ 115-140 kDa on Western blots of rat cortical homogenate, as well as a band of $M_r$ 93 kDa.

PC12 cells were grown in Dulbecco's modified Eagle's medium (DMEM, Flow Labs) containing 10% (v/v) fetal calf serum and 5% heat inactivated horse serum (GIBCO).

For metabolic labeling of PC12 cells, the cells were washed twice, removed from the dish by trituration, and the cells were suspended at $6 \times 10^6$ cells/ml in methionine-free DMEM, supplemented with 1 mCi/ml of [$^{35}$S]methionine (1200 Ci/mmol, NEN Products, Boston, Mass.) and 20 mM Hepes, pH 7.4 for 20 minutes. The cells were then diluted with 5-6 volumes of aerated complete medium (DMEM), containing excess methionine and 20 mM Hepes, pH 7.4, and chased for time periods of 0 to 135 minutes with additions as described. Test substances were added either at the start of the chase period (zero-time) or 35 minutes later. Cell viability, as determined by trypan blue exclusion, was greater than 90% at the start of the experiment and decreased less than 5% over 135 minutes of chase.

For lysis, the cells (0.2 ml) were diluted with 0.4 ml of lysis buffer (2 mM NaN$_3$ 150 mM NaCl, 100 mM Tris HCl, pH 7.4, containing 1% v/v NP40, 0.5% w/v sodium deoxycholate, 0.1% w/v NaDodSO$_4$ and 40 units/ml of trasylol) and placed on ice. After 20 minutes, samples were centrifuged at 10,000×g for 5 minutes, and the supernatants were used for immunoprecipitation. In some experiments, the cells were sometimes lysed with 1% NaDodSO$_4$, sonicated and boiled and used for immunoprecipitation. The results obtained with this procedure were virtually identical to those obtained using the standard procedure.

For immunoprecipitation, the 10,000×g supernatant was incubated for 1 hour at 4° C. with 3 μl of undiluted or affinity-purified rabbit anti-APP$_{645-695}$ in a total volume of 600 μl. Following the incubation, 75 μl of a 1:1 suspension of Protein A-Sepharose (Pharmacia LKB, Inc., Piscataway, N.J.) in lysis buffer was then added and the incubation was continued for another 30 minutes at 4° C. The insoluble complexes were washed three times with 100 mM Tris HCl, pH 7.4, containing 150 mM NaCl and 2 mM NaN$_3$ resuspended in solubilization buffer (62.5 mM Tris HCl, pH 6.8, 2% SDS, 5% 2-mercaptoethanol, 10% sucrose) and boiled. Proteins were separated by NaDodSO$_4$-PAGE and detected using quantitative fluorography with 1 M sodium salicylate. Protein bands were quantified either by densitometry of the autoradiograms, or by excising the radioactive bands and subjecting them to liquid scintillation spectrometry. APP$_{751}$ and APP$_{750}$ were the major APP isoforms in PC12 cells. Because these isoforms migrated very near each other on PAGE, they were sometimes quantified together and denoted APP$_{751/770}$. To quantify APP$_{695}$, computational methods were used (Crandall et al., 1987, *Anal. Biochem.*, 167:15). The effects observed for APP$_{695}$ were similar to those observed for APP$_{751/770}$. The 19 kDa peptide appeared to behave quantitatively similar to the 15 kDa peptide.

Peptide mapping of immunoprecipitated APP or in vitro translated APP was performed using *S. aureus* V8 protease (Miles Co., Elkhart, Ind.) according to the method of Huttner et al (1979, *Proc. Natl. Acad. Sci. USA*, 76:5402-5406).

Results

Figure 1A:
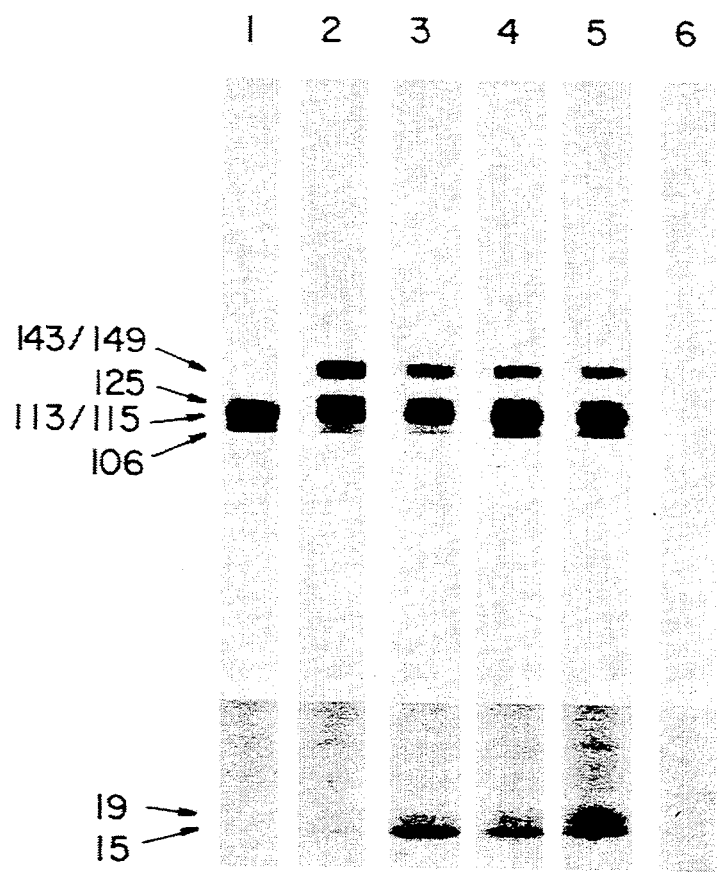
FIG. 1 are autoradiograms of PAGE gels from immunoprecipitates of [$^{35}$S]methionine labeled PC12 cells.
Figure 1B:

PC12 cells were incubated for 20 minutes in DMEM containing [$^{35}$S]methionine and subsequently chased for various periods in complete medium. Immunoprecipitation from lysates of such $^{35}$S-labeled cells with an antibody prepared against APP$_{645-695}$ yielded six protein bands of 149, 143, 125, 115, 113 and 106 kDa (FIG. 1A, lanes 1 and 2). These six proteins were not observed when the immunoprecipitation was carried out in the presence of 100 μM APP$_{645-695}$ peptide (FIG. 1A, lane 6). Furthermore, these six proteins exhibited similar peptide maps when digested with V8 protease, and the maps were similar to the maps observed using in vitro transcribed and translated human APP$_{695}$ cDNA (FIG. 1B), providing strong evidence that the immunoprecipitated protein bands are APP isoforms.

Changes in the relative amounts of the labeled bands were observed after different durations of the chase period. A possible precursor-product relationship was noted between the doublets of $M_r$ 113/115 and 143/149 kDa, as well as between the bands of $M_r$ 106 and 125 kDa (FIGS. 1 and 2). Based on the observations of Wiedemann et al, supra, the proteins of $M_r$ 143/149 and 125 kDa were identified as follows: $M_r$ 106, 113 and 115 kDa bands, the immature (N-glycosylated) forms of $APP_{695}$, $APP_{751}$ and $APP_{770}$, respectively; $M_r$ 125, 143 and 149 kDa, the mature (N- and O-glycosylated) forms of $APP_{695}$, $APP_{751}$ and $APP_{770}$, respectively.

Regulation of APP Processing by Protein-Kinase C

When PC12 cells were incubated with 1 μM PDBu during the chase period, no effect was observed on the rate of disappearance of labeled immature APP (FIG. 2A). However, the levels of labeled matured forms of APP decreased and the levels of labeled peptides of 15 kDa and 19 kDa were increased (FIGS. 2B,C). The 15 kDa and 19 kDA peptides were not observed when immunoprecipitation was carried out in the presence of 100 μM $APP^{645-694}$ peptide (FIG. 1A, lane 6), consistent with these proteins being COOH-terminal fragments of the mature APP. Another phorbol ester, PMA, produced effects similar to those of PDBU, while the inactive PBDu analogue, 4αPBDu was without effect. The decrease of labeled mature APP and concomitant increase of the labeled 15 kDa and 19 kDa peptides suggests a precursor-product relationship between these proteins. Presumably, the 15 kDa and 19 kDa peptides are proteolytic fragments of APP which remain associated with the cell after cleavage and secretion of the N-terminal domain. It will be of considerable importance to determine specific APP isoform from which the 15 kDa and 19 kDa peptides were derived. The data suggest that PKC activation increased the rate of processing of mature APP, leading to decreased recovery of the mature APP and increased recovery of proteolytic fragments.

1-(5-isoquinolinesulfonyl)-2-methylpiperazine dihydrochloride (H7) (100 μM), an inhibitor of several protein kinases including protein kinase C, produced a relative increase in the levels of mature APP (FIG. 2B). These observations are consistent with the idea that PKC stimulates the processing of mature APP. Moreover, H7, (100 μM) antagonized the effects of PDBU (1 μM) in decreasing the levels of labeled mature APP and increasing the levels of labeled 15 kDa and 19 kDa peptides.

A half-maximal effect of PDBu on the levels of labeled mature APP was observed at about 17 nM, consistent with other effects of PDBU known to be mediated by PKC. In order to examine the effect of activation of PKC on APP processing when the levels of mature APP neared maximal levels, PDBu (1 μM) was added after 35 minutes of chase. Rapid increases in the levels of labeled 15 kDa and 19 kDa peptides were observed (FIG. 3C), supporting the hypothesis that PDBu acts to increase the rate of processing of mature APP.

Regulation of APP Processing by Okadaic acid-sensitive Protein Phosphatases

Figure 4C:
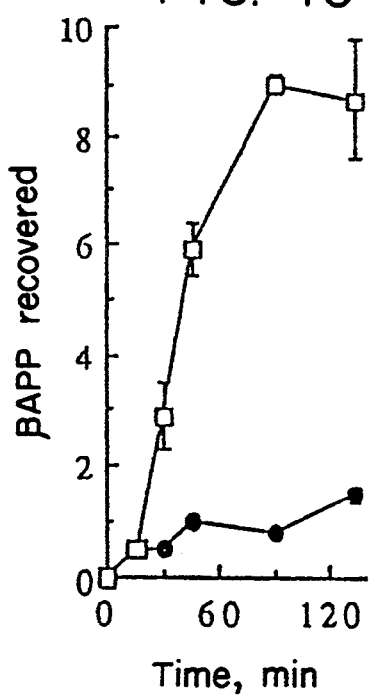
Figure 5C:
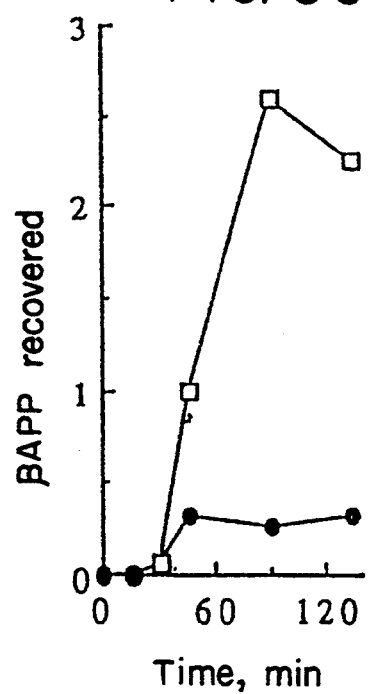

Addition of okadaic acid (1 μM) at the start of the chase increased the half-life of labeled immature APP, while the amount of labeled mature APP fell (FIGS. 4A,B). At the same time the labeled 15 kDa and 19 kDa APP peptides were increased (FIG. 4C). This suggests that okadaic acid, like PDBu, increases the rate of processing of mature APP, but, unlike PDBu, also affects APP processing at earlier stages. When okadaic acid (1 μM) was added with PDBu (1 μm) at the start of the chase, levels of the labeled 15 kDa and 19 kDa peptides were greatly increased (FIG. 1A, lane 5). Addition of okadaic acid after 35 minutes of chase, when mature APP neared maximal levels, led to a rapid increase in the levels of the labeled 15 kDa and 19 kDa peptides (FIG. 5C). These results support the hypothesis that okadaic acid acts to increase the rate of processing of mature APP. A half-maximal effect of okadaic acid on the levels of labeled immature and mature APP was observed at about 300 nM.

Applicants have confirmed that APP in PC12 cells matures over a period of 45 minutes (Wiedemann et al., 1989, Cell, 51, 115), and that can be processed via a lysosomal pathway (Cole et al, 1989, Neurochem. Res. 14:933).

Phorbol esters lead to an apparent stimulation in the rate of processing of mature APP and the formation of 15 kDa and 19 kDa peptides. One cannot exclude an effect of phorbol esters on the rate of catabolism of these peptides. These results suggest that PKC may regulate APP processing. The fact that H7, an inhibitor of PKC, leads to an apparent decrease in the basal rate of processing of APP supports the physiological significance of this reaction.

The effect of activators of PKC on the levels of the labeled 15 kDa and 19 kDa peptides is intriguing when examined in view of the known normal processing of APP. It has been reported that the extracellular portion of APP is normally secreted after APP is cleaved within the β/A4 domain (Sisodia et al., 1980, Science, 248:492–495). This means that normal APP processing precludes amyloidogenesis and, presumably, cerebral plaque formation. The 15 kDa and 19 kDa peptides have apparent molecular weights consistent with their containing the entire β/A4 sequence and therefore with their potentially being amyloidgenic.

Okadaic acid, a potent inhibitor of phosphatases 1 and, 2A, has been shown to increase net phosphorylation for many substrates in various experimental systems. Therefore, the effect of okadaic acid on APP processing cannot be attributed to any one kinase and may involve phosphorylation of APP by kinases distinct from those characterized previously, or may involve phosphorylation of other proteins involved in the regulation of APP maturation and processing.

The observations that PKC and potentially other protein kinases are involved in the regulation of normal and possibly altered processing of APP supports the possibility of a role of abnormal phosphorylation in the amyloidogenesis of Alzheimer's disease.

Example 2

The materials and methods used herein, including the [$^{35}$S]methionine pulse-chase procedure, have been reported (Caporaso et al., (1992). Proc. Natl. Acad. Sci. USA, 87:2252–2256). PDBu, 4α-PDBu, and okadaic acid were purchased from LC Services (Woburn, Mass.). When the effects of phorbol esters (1 μM) or okadaic acid (1 μM) were examined, drug was added at the start of the chase period. Control cells were treated with drug vehicle alone (0.05–0.15%) dimethyl sulfoxide, final concentration). The amounts of labeled APP holoproteins and APP fragments were quantitated as described. It should be noted that synthesis of labeled protein continued after the start of the chase and, therefore, that the values for the recovery of mature APP, secreted APP, and the carboxyl-terminal APP fragment are overestimated in absolute terms but accurate in relative terms.

Results

Domain-specific antibodies were employed to identify the APP species present in cell lysates and conditioned medium from metabolically labeled PC12 cells. Antibodies directed against the amino terminus (22C11) or against the carboxyl terminus (369A) of APP immunoprecipitated, from cell lysates, as described above.

Proteins with molecular masses of 109, 123, and 129 kDa were immunoprecipitated from conditioned medium using antibody 22C11, but no protein was recovered using antibody 369A, indicating that only amino-terminal APP fragments were present in the medium. Based upon earlier reports (Weidemann et al., 1989, *Cell*, 57:115-126; Buxbaum et al., 1990, *Proc. Natl. Acad. Sci. USA* 87:6003-6006) and the current results, it was concluded that the 109-, 123- and 129-kDa proteins are the secreted amino-terminal fragments of $APP_{695}$, $APP_{751}$, and $APP_{770}$, respectively.

Effects of Phorbol Ester on Maturation and Turnover of APP Holoprotein and on Recovery of the Carboxyl-Terminal APP Fragment.

Figure 6A:
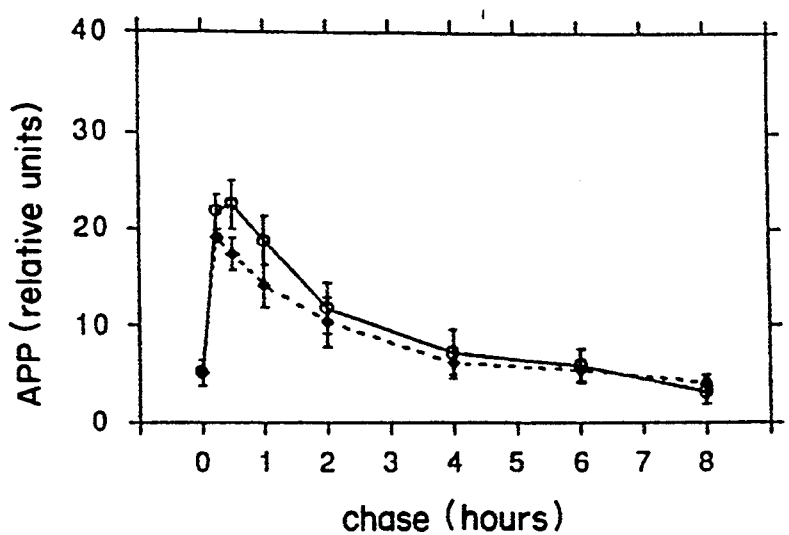
FIG. 6 depicts three graphs showing the recovery of different mature APP isoforms in intact cells in the presence or absence of PDBu.
Figure 6B:
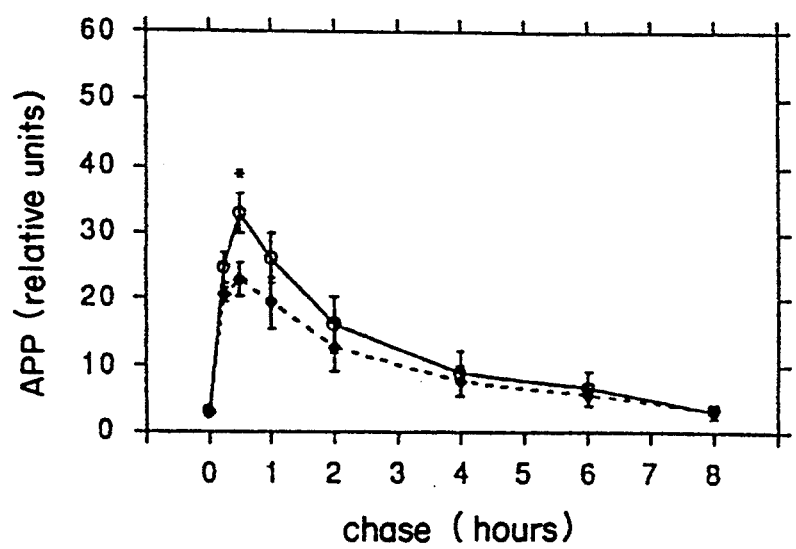
Figure 6C:
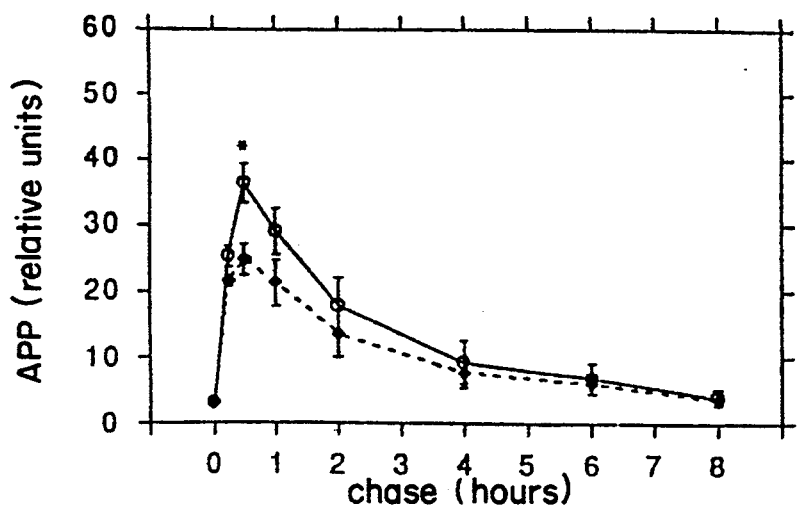

It has been demonstrated that treatment of PC12 cells with PDBu has no effect on APP maturation but results in more rapid turnover of mature APP and increased production of a carboxyl-terminal APP fragment. Those results were extended to differentiate among APP isoforms. Recovery of mature APP in intact cells was maximal at 30 minutes of chase and decreased thereafter (FIG. 6A-C). The recovery of mature APP in the presence of PDBu at 30 minutes of chase represented ~73% of that seen in control cells. By 8 hours of the chase period, the amounts of labeled mature APP isoforms had returned to the levels present at the start of chase.

Effect of Phorbol Ester on APP Secretion

Figure 7A:
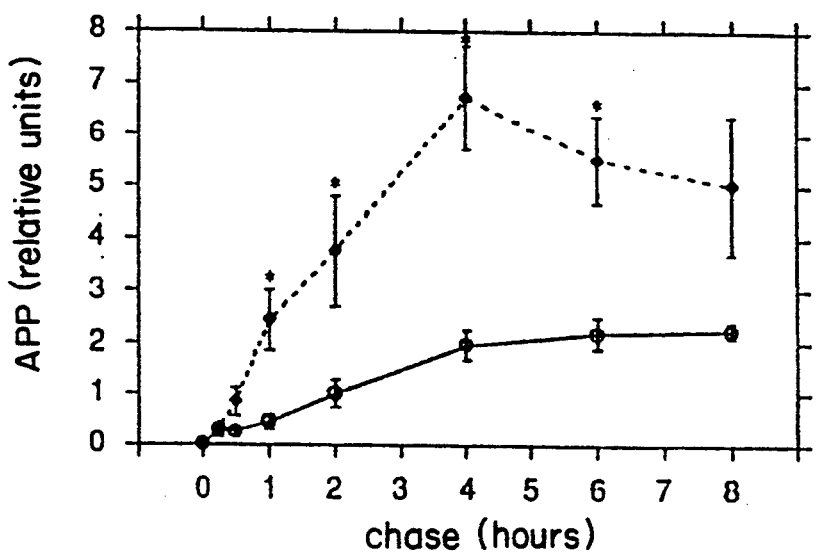
FIG. 7 depicts three graphs showing the recovery of different secreted amino-terminal APP isoform fragments in the presence or absence of PDBu.
Figure 7B:
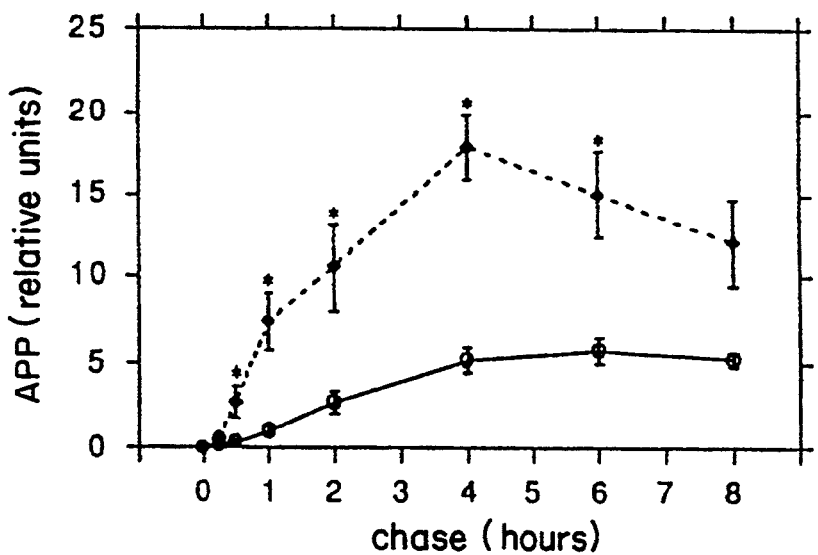
Figure 7C:
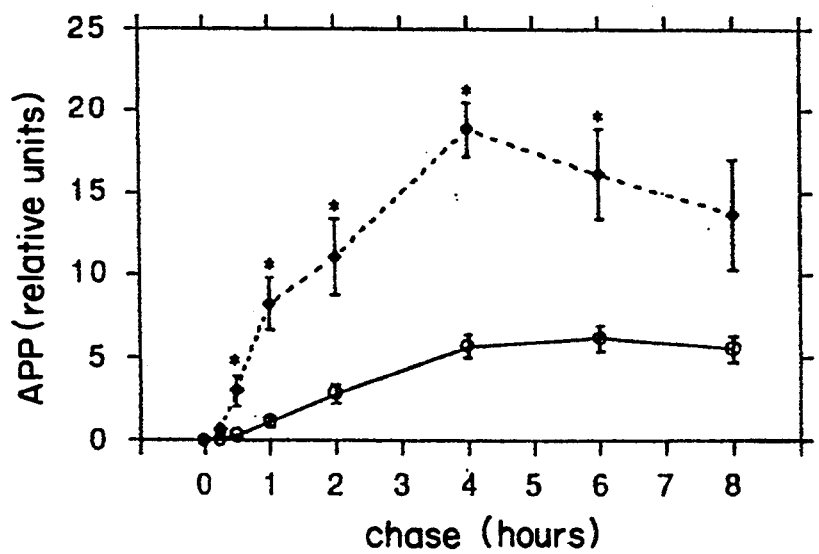
Figure 12:
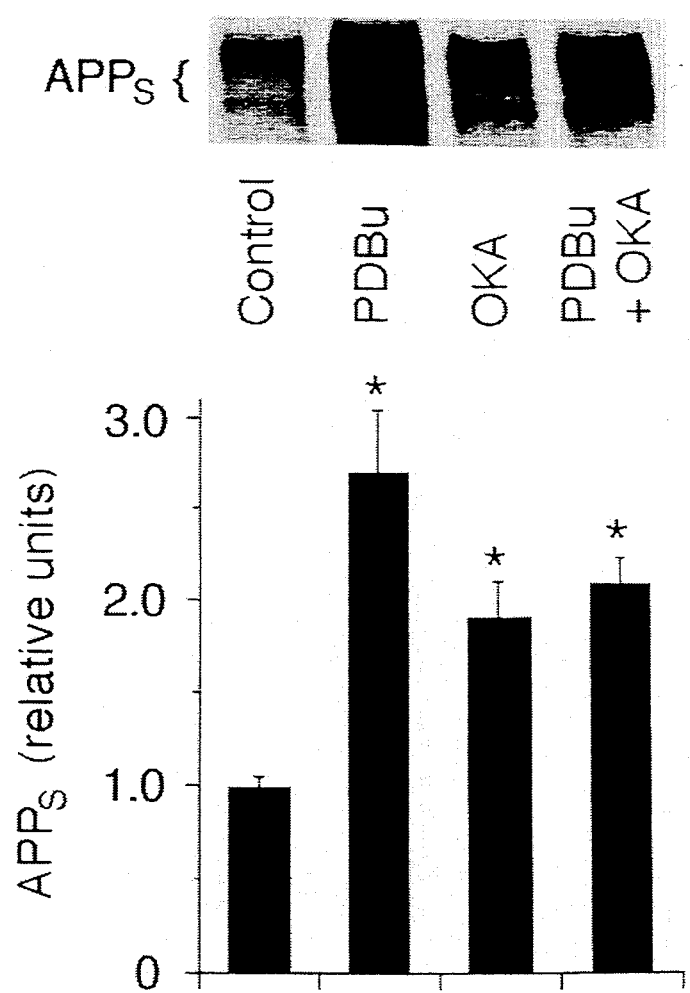
FIG. 12 is an autoradiogram and its graphic quantification of the effects of PDBu and okadaic acid on secreted APP.

As phorbol esters were found to cause an increase in mature APP turnover, Applicants examined whether this effect was associated with an alteration in the rate and/or amount of APP secretion. PDBu treatment was found to cause a dramatic increase in APP secretion. When the amounts of secreted APP were quantified, the relative phorbol ester effects were approximately the same among APP isoforms (FIGS. 7, 12). In both untreated and treated cells, APP secretion continued up to 4 hours of the chase period. From 4 to 8 hours, the amount of secreted APP fragments recovered from the medium remained unchanged or decreased slightly. The amount of secreted APP in the medium decreased with time when the 4 hours conditioned medium was incubated in the absence of cells, indicating that the disappearance was attributable to proteolysis.

There was up to a 3-fold accumulation of secreted APP in the medium of PDBu-treated cells relative to control levels. Phorbol ester caused an increase in the rate of accumulation and in the absolute amount of secreted APP. At 4 hours of chase, ~14% of the labeled APP present at the start of chase was recovered as secreted amino-terminal APP fragments from the medium of control cells, whereas ~43% was recovered from the medium of PDBu-treated cells. This indicates that under control conditions, a relatively small pool of APP was cleaved within the $\beta/A_4$ amyloid domain to produce secreted APP. The majority of APP molecules were presumably degraded by an intracellular proteolytic pathway unassociated with secretion.

When the difference between mature APP holoprotein recovered from PDBu-treated and untreated cells (at 30 min of chase) was compared to the difference between secreted APP fragments recovered from the medium of PDBu-treated and untreated cells (at 4 hours of chase), a close correlation was found ($27\pm6$ versus $31\pm3$ relative units, respectively). Thus, the phorbol ester-stimulated turnover of mature APP holoprotein could be quantitatively accounted for by enhanced APP secretion.

Absence of Effect of Inactive Phorbol Ester on APP Secretion

Figure 8A:
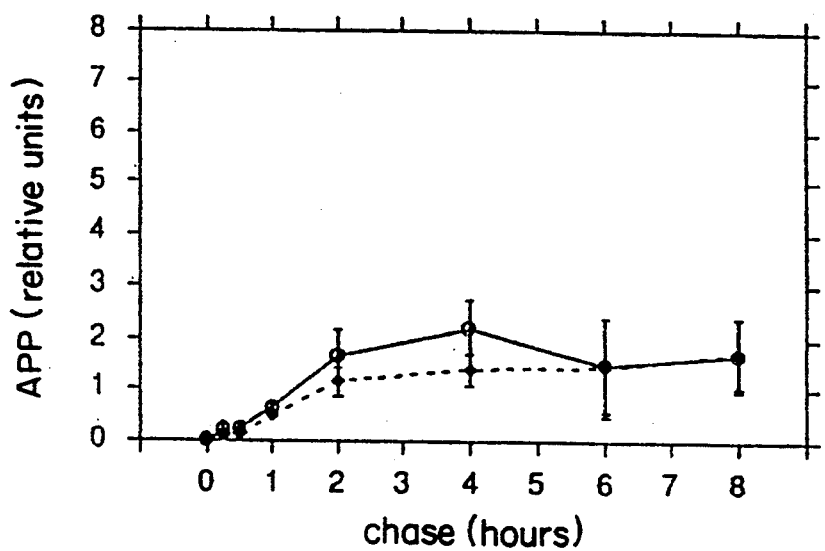
FIG. 8 depicts three graphs showing the recovery of secreted amino-terminal APP fragments in the presence or absence of 4α-PDBu.
Figure 8B:
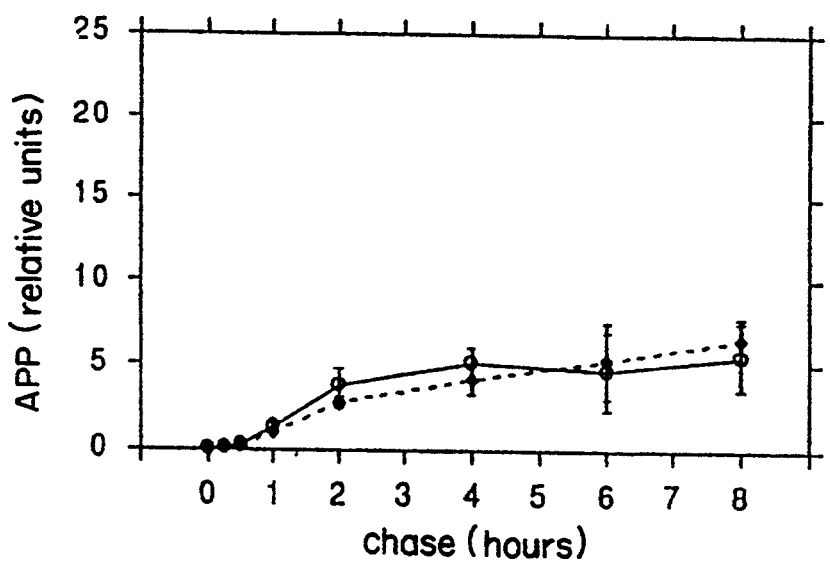
Figure 8C:
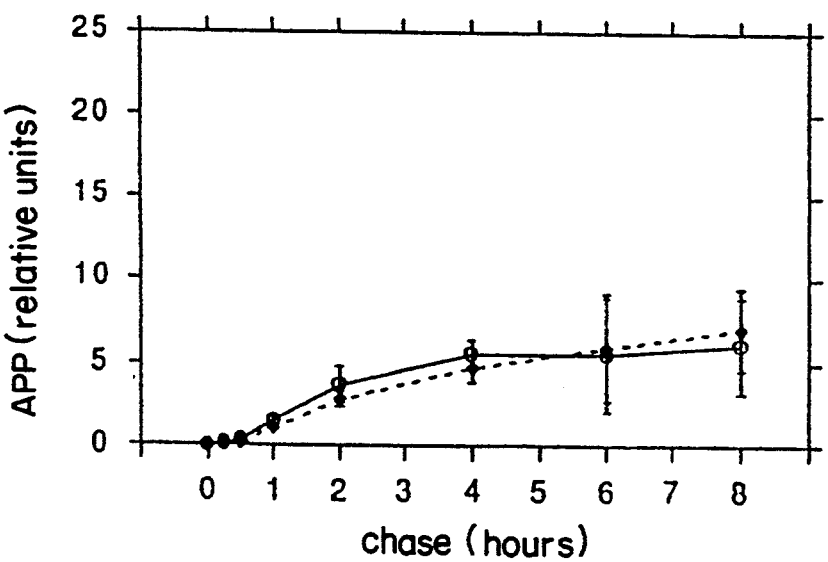
Figure 9:
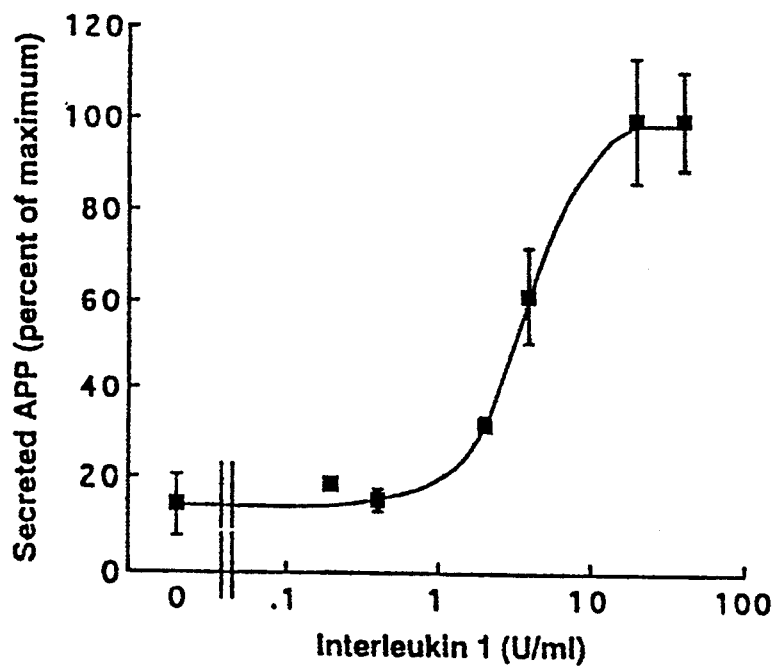
FIG. 9 is a graph showing regulation of APP secretion by IL-1.

As a control for the specificity of PDBu activation of PKC, cells were also treated with the inactive analog, 4α-PDBu. There was virtually no effect on APP maturation or holoprotein turnover or on APP secretion (FIG. 8) in the presence of 4α-PDBu relative to cells treated with vehicle alone.

Effect of Combined Treatment with Phorbol Ester and Okadaic Acid on APP Secretion Combined treatment with PDBu and okadaic acid, an inhibitor of protein phosphatases 1 and 2A, was previously found to increase recovery of APP carboxyl-terminal fragments. Therefore, the effect of combined treatment on APP secretion was also examined. Cells treated for 1 hour with okadaic acid alone secreted more APP than untreated cells but less APP than cells treated with PBDu (FIG. 12). When cells were treated with both PDBu and okadaic acid, APP secretion at 1 hour was greater than APP secretion in cells treated with PDBu or okadaic acid alone, in PC12 cells, but somewhat less in CHO cells (FIG. 12).

Although combined treatment with PBDu and okadaic acid produces a carboxyl-terminal fragment that migrates on SDS/polyacrylamide gels more slowly than the 15-kDA species (FIG. 1), no evidence of truncated secreted APP fragments was found. Furthermore, no treatments resulted in the detection of cleaved amino-terminal APP fragments in cell lysates.

Example 3

Acetylcholine chloride, carbachol, bethanechol chloride, and atropine sulfate were purchased from Research Biochemicals (Natick, Mass.); recombinant human IL-1β ($>10^7$ units/mg) and thrombin (from human plasma), from Boehringer Mannheim; IL-1ra, from R & D Systems (Minneapolis(; phorbol 12,13-dibutyrate, from LC Services (Woburn, Mass.); and chloroquine, from Sigma. All media and animal sera for culturing cells were purchased from GIBCO/BRL.

Human umbilical vein endothelial cells (HUVEC) were prepared and maintained as described (E. A. Jaffe, *J. Clin. Invest.* 52:2745-2746) and used at the second or third passage. The Hs 683 cell line was purchased from American Type Culture Collection and maintained in Dulbecco's modified Eagle's medium containing 10% (vol/vol) fetal bovine serum (FBS); SH-SY5Y cells (J. L. Biedler et al., *Cancer Res.* 33:2643-2652) were the gift of J. Biedler (Memorial Sloan-Kettering Cancer Center, N.Y.) and were maintained in 1:1 (vol/vol) minimal essential medium/Ham's F-12 medium containing 15% FBS. PC12 cells, stably transfected with the $M_1$ receptor (R. Pinkas-Kramarski et al., *J. Neurochem.*, in press) were maintained in RPMI 1640 containing 10% FBS and 5% horse serum.

Pulse-chase labeling for $PC12M_1$ and SH-SY5Y cells was carried out as described, with the addition of 1% fetal bovine serum to the medium; for HUVEC and for Hs 683 cells, pulse-chase labeling was performed identically except that labeling was performed on cell monolayers in 12-well culture dishes (Corning) with 200 μl of medium per well. Metabolic labeling was carried out for 20 minutes followed by a chase period of 0–240 minutes. The chase was initiated by the addition of an equal volume of medium containing excess unlabeled methionine. Two minutes later, test compounds dissolved in medium were added. Thus, the effects observed were attributable to changes in APP metabolism rather than APP transcription. Following incubation, APP was purified from cell lysates by immunoprecipitation with an anti-APP COOH-terminal antibody (369) and from conditioned medium with an anti-APP NH$_2$-terminal antibody (22C11). Purified APP was subjected to PAGE and quantified by using a PhosphorImager (Molecular Dynamics, Sunnyvale, Calif.). ANOVA followed by Bonferroni t test was used to determine the significance of observed differences.

Results

APP Turnover in Cultured Cells

To identify physiological regulators of APP metabolism, an analysis of the regulation of APP processing and secretion by different first messengers in various cell types was undertaken. The following cells were used herein: (i) HUVEC; (ii) human glioma cells (Hs 683); (iii) human neuroblastoma cells (SH-SY5Y); and (iv) PC12 cells transfected with the M$_1$ receptor (PC12M$_1$). In metabolically labeled HUVEC and in labeled Hs 683, SH-SY5Y, and PC12M$_1$ cells, APP was first detected as lower molecular weight proteins which then matured (with a concomitant increase in apparent molecular weight), the mature molecules in turn serving as substrates for cleavage and secretion. As was previously found for PC12 cells, mature APP reached maximal levels at between 45 and 60 minutes, while secreted proteins reached maximal levels after 3 hours. Secreted APP could not be immunoprecipitated by an antibody against the cytoplasmic domain of APP, indicating that secreted APP had been cleaved normally.

Regulation of APP Metabolism by Phorbol Dibutyrate and Chloroquine

In PC12 cells, APP can either undergo protein kinase C-regulated section or be degraded in a chloroquine-sensitive intracellular compartment. To confirm that both pathways were present in the four cell types used in these studies, we incubated metabolically labeled cells were incubated for 60 minutes in the absence or presence of either 1 μM phorbol dibutyrate or 50 μM chloroquine. In all cell types under control conditions, a small but detectable amount of APP was secreted in this time period. Phorbol dibutyrate enhanced the levels of secreted APP by 3- to 7-fold in all cell types (see Table 1, below). The increased secretion of APP was accompanied by a decrease in the levels of mature, cell-associated APP.

TABLE 1

Regulation of APP secretion by phorbol dibutyrate

| Cell Type | Control | PDBu |
|---|---|---|
| SH-SY5Y | 1.00 ± 0.09 | 2.82 ± 0.45* |
| PC12M$_1$ | 1.00 ± 0.19 | 4.30 ± 0.04* |
| HUVEC | 1.00 ± 0.05 | 6.79 ± 0.51* |
| Hs 683 | 1.00 ± 0.10 | 7.08 ± 1.55* |

The indicated cell types were incubated for 60 minutes in the absence or presence of 1 μM of phorbol dibutyrate (PDBu). Secreted APP was then analyzed as described in text. Within each experiment, incubations were carried out in triplicate, and data were normalized to the average amount of APP recovered under control conditions. The results shown represent the means ± SEM of two or three experiments performed in duplicate or triplicate, $P < 0.003$.

Incubation with chloroquine resulted in significantly higher (approximately 2-fold) amounts of mature APP recovered in the cell lysate at 60 minutes of chase, compared with control cells. Chloroquine had no significant effect on secretion by these cells. These data indicate that, in these cells, two pathways exist for APP metabolism and that first messengers that activate protein kinase C can regulate APP processing in these cells.

Cholinergic Agonists Regulate APP Processing and Secretion

The effects of the cholinergic agonists acetylcholine, carbachol, and bethanechol on APP metabolism were studied. These compounds activate protein kinase C in some cells. When PC12 cells that had been transfected with the M$_1$ receptor (PC12M$_1$) were incubated with the cholinergic agonist acetylcholine (1 mM), there was a more than 3-fold increase in the levels of secreted APP during 60 minutes of chase (see Table 2, below) compared with control cells. Carbachol (1 mM), and the muscarinic agonist bethanechol (1 mM), stimulated secretion by 4- to 6-fold (see Table 2, below). The effects of 1 mM bethanechol on APP secretion were blocked by the muscarinic antagonist atropine (100 μM) (see Table 2, below).

Carbachol and bethanechol stimulated APP secretion in human neuroblastoma cells (SH-SY5Y) and human glioma cells (Hs 683) by 60–100% (see Table 2, below), supporting the idea that the effects of muscarinic agonists on APP metabolism are of physiological relevance. In HUVEC no significant effect of bethanechol on APP secretion was observed.

TABLE 2

Regulation of APP secretion by cholinergic agonists and antagonists

| Cell Type | Treatment | Relative Secretion |
|---|---|---|
| PC12M$_1$ | Control | 1.00 ± 0.01 |
| | Acetylcholine (1 mM) | 3.59 ± 0.61* |
| | Carbachol (1 mM) | 5.73 ± 0.83* |
| | Bethanechol (1 mM) | 4.29 ± 0.67* |
| | Bethanechol (1 mM) + atropine (100 μM) | 1.30 ± 0.28$^{NS}$ |
| SH-SY5Y | Control | 1.00 ± 0.28 |
| | Carbachol (1 mM) | 1.61 ± 0.10* |
| Hs 683 cells | Control | 1.00 ± 0.10 |
| | Bethanechol (1 mM) | 2.07 ± 0.12* |

Figure 10:
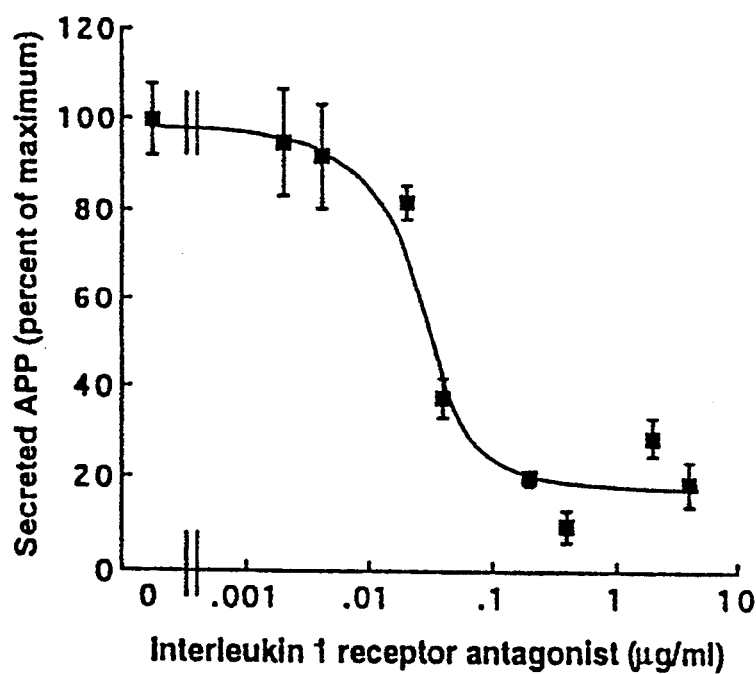
FIG. 10 is a graph showing regulation of APP secretion by IL-1ra in the presence of IL-1.
Figure 11B:
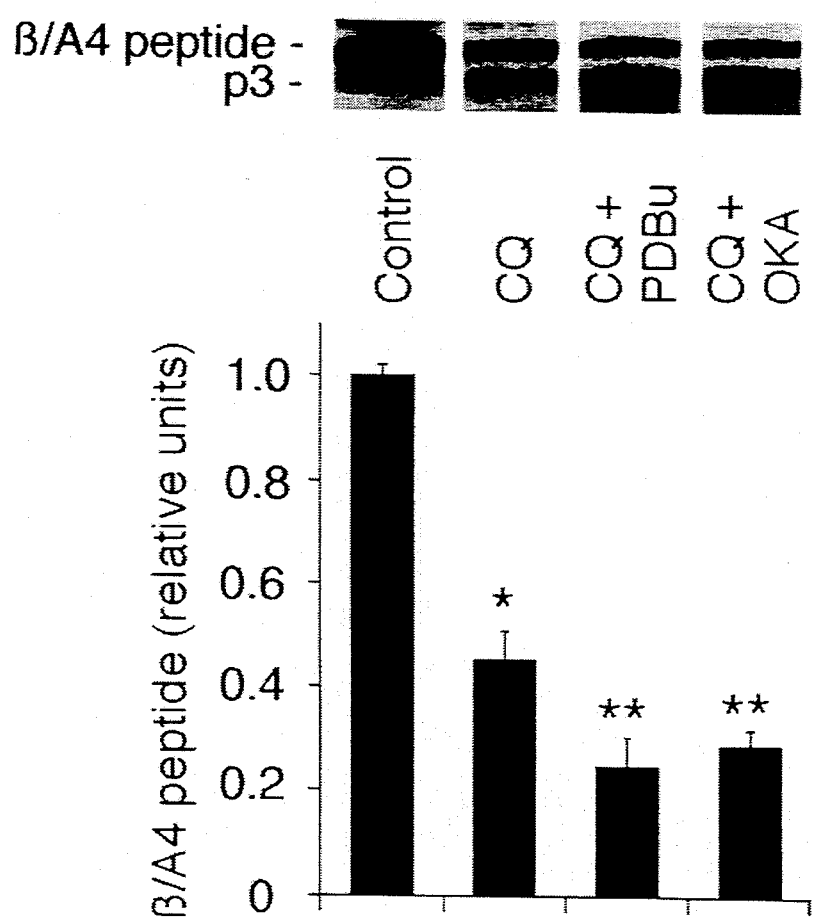
FIG. 11 depicts two autoradiograms and the graphic quantifications of the recovery of $\beta/A_4$ peptide.

The indicated cell types were incubated for 60 minutes in the absence or presence of the indicated test compounds. Secreted APP was then analyzed as described in text. Within each experiment, incubations were carried out in triplicate, and data were normalized to the average amount of APP recovered under control conditions. The results shown represent the means ± SEM of two or three experiments, $P < 0.003$, NS, not significant, $P = 0.21$ IL-1 Regulates APP Processing and Secretion IL-1 can increase APP expression in HUVEC (D. Goldgaber et al., 1989, Proc. Natl. Acad. Sci. USA 86:7606–7610) and other cells (R. J. Donnelly et al., 1990, Cell. Mol. Neurobiol. 10:485–495; R. P. Smith et al., 1990, Science 248:1126–1128) by what is probably a protein kinase C-mediated mechanism (Goldgaber et al., supra). When metabolically labeled HUVEC were incubated for 60 minutes in the presence of IL-1 (20 units/ml), APP secretion increased more than 3-fold (see Table 3, below) compared with control cells. The effect of various concentrations of IL-1 on APP secretion is shown in FIG. 10. A half-maximal effect (ED$_{50}$) was observed at about 3.2 units/ml. The effect of IL-1 was antagonized by IL-1ra; IL-1ra blocked the effect of 20 units of IL-1 per ml (FIG. 11).

Glial cells may be involved in the brain's response to injury and can respond to IL-1 (see ref. 2 - Griffin et al., 1989, *Proc. Natl. Acad. Sci. USA* 86:7611–7615); as a model for this phenomenon, the effects of IL-1 on human glioma (Hs 683) cells were also studied. IL-1 (20 units/ml) increased APP secretion in these cells by more than 2-fold (see Table 3, below). In SH-SY5Y and PC12M$_1$ cells, IL-1 did not lead to significant increases in APP secretion.

Thrombin, like IL-1, is involved in the acute-phase response and has been shown to stimulate APP secretion in platelets (Smith et al., (1990), *Science* 248:1126–1128: Gardella, et al. (1990), *Biochem. Biophys. Res. Commun.* 173:1292–1298). Because other cells involved in the acute-phase response (including HUVEC) are known to respond to thrombin, the effects of 2 units of thrombin per ml on APP secretion were characterized. In both HUVEC and Hs 683 cells, this compound increased APP secretion by about 2-fold (see Table 3, below). In SH-SYSY and PC12M$_1$ cells, thrombin did not lead to significant increases in APP secretion.

TABLE 3

| Regulation of APP secretion by interleukin 1 and thrombin | | |
|---|---|---|
| Cell Type | Treatment | Relative Secretion |
| HUVEC | Control | 1.00 ± 0.05 |
| | IL-1 (20 U/ml) | 3.66 ± 0.26* |
| | Thrombin (2 U/ml) | 1.91 ± 0.19* |
| Hs 683 | Control | 1.00 ± 0.10 |
| | IL-1 (20 U/ml) | 2.57 ± 0.26* |
| | Thrombin (2 U/ml) | 2.21 ± 0.19* |

Cells were incubated for 60 minutes in the absence or presence of the indicated test compounds. Secreted APP was then analyzed as described in text. Within each experiment, incubations were carried out in triplicate, and data were normalized to the average amount of APP recovered under control conditions. The results shown represent the means ± SEM of three to five experiments, $P < 0.003$, U, units.

Example 4

Pulse-chase labeling of CHO cells, stably expressing human APP$_{695}$ was carried out on confluent cell monolayers in 6-well culture dishes (Corning) with 1 ml of methionine-free DMEM, supplemented with 1 mCi of [$^{35}$S]methionine (EXPRE$^{35}$S$^{35}$S, NEN). Metabolic labeling was carried out for 2 hours, followed by a chase period of 2 hours. The chase was initiated by replacing the labeling medium with DMEM containing excess unlabeled methionine. Two minutes after the start of the chase, the indicated test compounds were added to maximize the probability that any observed effects were attributable to changes in APP metabolism rather than APP transcription. Following incubation, conditioned medium was centrifuged for 5 minutes at 10,000×g. $\beta/A_4$ peptide and p3 were immunoprecipitated using an anti-$\beta A4^{1-40}$ antibody (4G8), and APP$_S$ was immunoprecipitated using an anti-APP NH$_2$-terminal antibody (22C11). Immuno-precipitated APP fragments were subjected to SDS-PAGE (10–20% Tris-tricine gels for $\beta/A_4$ peptide and p3, 6% Tris-glycine gels for APP$_S$), and autoradiographed and quantified using a PhosphorImager (Molecular Dynamics, Sunnyvale, Calif.). ANOVA followed by Fisher's post hoc analysis was used to determine the significance of observed differences.

The protocols used for CHO cells stably expressing APP$_{751}$ or mutant APP$_{751}$, and for Hs 683 cells were identical.

Results

When the medium of metabolically labeled CHO cells, stably transfected with cDNA encoding the 695-amino-acid isoform of APP (APP$_{695}$) was subjected to immunoprecipitation using an antibody (4G8) raised against a synthetic peptide corresponding to residues 1–40 of $\beta/A_4$ peptide ($\beta/A_4^{1-40}$), two small peptide bands with M$_r$ of 3- and 2-kDa were observed. These peptides had migration rates similar to those of two peptides that had been identified previously as $\beta/A_4$ peptide and p3. p3 was shown to be a $\beta/A_4$ peptide fragment deleted of the first 16–17 amino acids. On the basis of these similarities in migration rates, and similarities in immunochemical properties, it was concluded that the two small peptide bands of M$_r$ 3- and 2-kDa represent $\beta/A_4$ peptide and p3.

Production of $\beta A_4$ Peptide is Regulated by Protein Phosphorylation

The levels of $\beta/A$ peptide decreased dramatically when the cells were incubated with either phorbol dibutyrate (PDBu), okadaic acid, or both compounds together (FIG. 11a). Under the same conditions, the levels of p3 apparently rose by 30–50% (FIG. 11a); however, quantification was difficult because p3 was poorly resolved from a non-specific band.

Chloroquine Regulates $\beta/A_4$ Peptide Production

Chloroquine and ammonium chloride, which neutralize acidic organelles thereby inhibiting their acid-dependent hydrolases, decrease the levels of the $\beta/A_4$ peptide recovered from conditioned medium of cultured cells. Incubating labeled cells for 2 hours in the presence of chloroquine (50 $\mu$g/ml) alone decreased the levels of $\beta/A_4$ peptide recovered in cell culture supernatants (FIG. 11b), consistent with previous experiments. Incubating cells with chloroquine together with either PDBu or okadaic acid led to decreases in $\beta/A_4$ peptide levels which were significantly greater than the decreases observed in the presence of chloroquine alone (FIG. 11b) or of PDBu or okadaic acid alone.

When cells were incubated in the absence or presence of PDBu, okadaic acid, or chloroquine, alone or in combination, and the cell lysates then examined for $\beta/A_4$ peptide, none was detected. These results indicate that, in these cells, either $\beta/A_4$ peptide is formed extracellularly or that it is secreted very efficiently upon its intracellular formation. In either case, the data indicate that protein phosphorylation regulates $\beta/A_4$ peptide production, rather than secretion.

The effects of PDBu and okadaic acid on $\beta/A_4$ peptide production from endogenous APP in a human glioma cell line (Hs 683) were also characterized. Incubating H3 683 cells with PDBu or okadaic acid decreased the production of $\beta/A_4$ peptide (Table 4a) in a manner similar to that observed for transfected CHO cells, supporting the physiological significance of the observations with the transfected cells.

It was recently reported that a mutant form of APP (APP[K$^{595}\rightarrow$N; M$^{596}\rightarrow$L]) is associated with increased $\beta/A_4$ peptide production. When CHO cells, stably transfected with cDNA encoding for either wild-type APP$_{751}$ or mutant APP$_{751}$ (APP$^{595}\rightarrow$N; M$^{596}\rightarrow$L] were incubated with 1 $\mu$m PDBu, there was a significant decrease in the levels of $\beta/A_4$ peptide recovered from the medium (Table 4b). These results indicate that protein phosphorylation regulates $\beta/A_4$ peptide production from APP$_{751}$ as well as from APP$_{695}$, and that even the elevated level of $\beta/A_4$ peptide production associated with APP[$K^{595} \rightarrow N$; $M^{596} \rightarrow L$] is sensitive to regulation by protein phosphorylation. PDBu also inhibited $\beta/A_4$ peptide production from cells expressing any of three other mutations in (APP$_{751}$ [$E^{618} \rightarrow Q$], APP$_{751}$ [$V^{642} \rightarrow I$], and APP751 [$V^{642} \rightarrow P$]), each of which is associated clinically with abnormal cerebral $\beta/A_4$ peptide deposition (Table 4b).

TABLE 4

Production of $\beta/A_4$ peptide is regulated by protein phosphorylation.

(a) Hs 683 cells

| TREATMENT | $\beta/A_4$ PEPTIDE (RELATIVE UNITS) |
|---|---|
| Control | 1.00 ± 0.029 |
| PDBu, 1 μM | 0.50 ± 0.083* |
| Okadaic acid, 2.5 μM | 0.55 ± 0.052* |

(b) CHO cells stably expressing wild-type or mutant APP$_{751}$

| | CONTROL | $\beta/A_4$ Peptide (relative units) PDBu |
|---|---|---|
| Wild-type APP$_{751}$ | 1.00 ± 0.075 | 0.53 ± 0.033* |
| APP $_{751}$[$E^{618} \rightarrow Q$] | 1.00 ± 0.086 | 0.32 ± 0.073* |
| APP$_{751}$[$V^{642} \rightarrow I$] | 1.00 ± 0.143 | 1.35 ± 0.051* |
| APP$_{751}$[$V^{642} \rightarrow P$] | 1.00 ± 0.061 | 0.30 ± 0.070* |
| APP$_{751}$[$K^{595} \rightarrow N$: $M^{596} \rightarrow L$] | 1.00 ± 0.045 | 0.37 ± 0.079* | a. $\beta/A_4$ peptide was immunoprecipitated from the medium of metabolically labeled Hs 683 cells. Results are the means ± SEM of 3 experiments performed in duplicate or triplicate. *, different from control ($p < 0.05$).
b. $\beta/A_4$ peptide was immunoprecipitated from the medium of metabolically labeled CHO cells, stably expressing either wild-type or mutant APP$_{751}$. Control, no additions: PDBu, 1 μM. Results are the means ± SEM of 3 experiments performed in triplicate. *, different from control ($p < 0.001$).

The effects of PDBu and okadaic acid on the production of APP$_S$, the secreted form of APP, were opposite to those observed for $\beta/A_4$ peptide; thus, treatment of cells with PDBu, okadaic acid, or both compounds together, significantly increased production of APP$_S$ (FIG. 12). These effects on APP$_S$ are consistent with observations made in other cell types. Under these conditions, the levels of p3 increased in the medium (FIG. 11a), consistent with the idea that p3 is derived from the alpha-secretory pathway.

The reciprocal effects of increased protein phosphorylation on APP$_S$ production and $\beta/A_4$ peptide production are consistent with the idea that APP$_S$ and $\beta/A_4$ peptide may be derived from two competing pathways of APP metabolism. APP is processed by at least two pathways: (a) a non-amyloidogenic α-secretory pathway, in which the extracellular portion of APP (APP$_S$) is released into the extracellular space and (b) an alternative pathway which generates the $\beta/A_4$ peptide. The ability of phorbol esters and okadaic acid to reduce the formation of $\beta/A_4$ peptide may be attributed to the diversion of APP from this alternative pathway to the α-secretory pathway. Lysosomotropic agents, including chloroquine and ammonium chloride, can inhibit $\beta/A_4$ peptide production, and it is possible that the alternative pathway leading to the formation of $\beta/A_4$ peptide involves acidic, intracellular, compartments. The fact that PDBu (or okadaic acid) plus chloroquine gave a larger inhibition of $\beta/A_4$ peptide production than either compound alone is consistent with the hypothesis that these compounds act at different sites of $\beta/A_4$ peptide production.

Compounds which stimulate APP$_S$ production thus provide a way to inhibit $\beta/A_4$ peptide production in the brain. Such compounds include a variety of neurotransmitters and hormones known to act through the phospholipase C/protein kinase C cascade, for example, muscarinic cholinergic agonists and interleukin 1. These compounds, along with pharmaceutical agents which increase protein kinase C activity or decrease protein phosphatase 1 or 2A activity, can be utilized to slow the development of Alzheimer disease.

It will be appreciated that the instant specification and examples are set forth by way of illustration and not limitation, and that various modifications and changes may be made without departing from the spirit and scope of the present invention.

What is claimed is:

1. A method of regulating phosphorylation of proteins that control the processing of APP, tau and neurofilament proteins comprising introducing an effective amount of at least one modulator of protein kinase or phosphatase, said modulator capable of controlling the proteolytic processing or function of said proteins.

2. A method according to claim 1 wherein said modulator is a direct or indirect modulator of protein kinase activity.

3. A method according to claim 2 wherein said direct or indirect modulator of protein kinase activity is selected from the group consisting of phorbol esters, indolactam, mezerin, diacylglycerol, cAMP, cGMP, and their analogs, forskolin, activators or inhibitors of adenylate and guanylate cyclase, activators or inhibitors of phospholipase C, and compounds increasing intracellular calcium.

4. A method according to claim 3 wherein said phorbol ester is selected from the group consisting of phorbol-12,13-dibutyrate, phorbol 12-myristate 13-acetate and their analogs.

5. A method according to claim 3 wherein the indolactam is (-)-7-octylindolactam V.

6. A method according to claim 2 wherein said indirect modulator of protein kinases is an agonist or antagonist of receptors for intercellular messengers which are known to modulate protein kinases, said receptors selected from the group consisting of adenosine, adrenoreceptors, angiotensin, atrial natriuretic peptide, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin, vasopressin and oxytocin, and VIP, modulators of and calcium or potassium ion channels.

7. A method according to claim 2 wherein said kinase modulator is selected from the group consisting of staurosporine; auranofin; N-(6-aminohexyl)-1-naphthalensulfonamide hydrochloride (W5); N-4(4-aminobutyl)-2-naphthalenesulfonamide hydrochloride (W12); N-(-4-aminobutyl)-5-chloro-2-naphthalenesulfonamide hydrochloride (W13); N-(6-aminohexyl)-5-chloro-1-naphthanesulfamide hydrochloride (W7); 1-(5-isoquinolinesulfonyl)-2-methylpiperazine dihydrochloride (H7); N-(2-(methylamino)ethyl]-3-isoquinolinesulfonamide dihydrochloride (H8); N-(2-aminoethyl)-5-isoquinolinesulfonamide (H9); N(2-guanidinoethyl)-5-isoquinoline-sulfonamide hydrochloride (HA1004); sphingosine and tyrphostin.

8. A method according to claim 1 wherein said modulator is a direct or indirect modulator of protein phosphatase activity.

9. A method according to claim 8 wherein said direct or indirect modulator of protein phosphatase activity is a selected from the group consisting of okadaic acid, calyculin-A, vanadate, and their analogs, FK506, cyclosporin, and compounds increasing intracellular calcium.

10. A method according to claim 8 wherein said indirect modulator of protein phosphatase is an agonist or antagonist of receptors for intercellular messengers which are known to modulate protein phosphatases, said receptors selected from the group consisting of adenosine, adrenoreceptors, angiotensin, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thomkin vasopressin and oxytocin, VIP, and modulators of calcium or potassium ion channels.

11. A method of inhibiting production of Alzheimer-type amyloidosis in a mammal comprising administering to said mammal in need of treatment an effective amount of at least one modulator of protein kinase or phosphatase, said modulator capable of controlling the proteolytic processing or function of proteins found in intracellular neurofibrillary tangles and extracellular amyloid plaques.

12. A method according to claim 11 wherein said modulator is a direct or indirect modulator of protein kinase activity.

13. A method according to claim 12 wherein said direct or indirect modulator of protein kinase activity is selected from the group consisting of phorbol esters, indolactam, mezerin, diacylglycerol, cAMP, cGMP, and their analogs, forskolin, activators or inhibitors of adenylate and guanylate cyclase, activators or inhibitors of phospholipase C, and compounds increasing intracellular calcium.

14. A method according to claim 13 wherein said phorbol ester is selected from the group consisting of phorbol-12,13-dibutyrate, phorbol 12-myristate 13-acetate and their analogs.

15. A method according to claim 13 wherein the indolactam is (-)-7-octylindolactam V.

16. A method according to claim 12, wherein said indirect modulator of protein kinases is an agonist or antagonist of receptors for intercellular messengers known to modulate protein kinases, said receptors selected from the group consisting of adenosine, adrenoreceptors, angiotensin, atrial natriuretic peptide, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin, vasopressin and oxytocin, VIP, and modulators of potassium or calcium ion channels.

17. A method according to claim 12 wherein said kinase modulator is selected from the group consisting of staurosporine; auranofin; N-(6-aminohexyl)-1-naphthalensulfonamide hydrochloride (W5); N-4(4-aminobutyl)-2-naphthalenesulfonamide hydrochloride (W12); N-(-4-aminobutyl)-5-chloro-2-naphthalenesulfonamide hydrochloride (W13); N-(6-aminohexyl)-5-chloro-1-naphthanesulfamide hydrochloride (W7); 1-(5-isoquinolinesulfonyl)-2-methylpiperazine dihydrochloride (H7); N-(2-(methylamino)ethyl]-3-isoquinolinesulfonamide dihydrochloride (H8); N-(2-aminoethyl)-5-isoquinolinesulfonamide (H9); N(2-guanidinoethyl)-5-isoquinoline-sulfonamide hydrochloride (HA1004); sphingosine and tyrphostin.

18. A method according to claim 12 wherein said modulator is a direct or indirect modulator of protein phosphatase activity.

19. A method according to claim 18 wherein said direct or indirect modulator of protein phosphatase activity is a selected from the group consisting okadaic acid, calyculin-A, vanadate, and their analogs, FK506, cyclosporin, and compounds increasing intracellular calcium.

20. A method according to claim 19 wherein said indirect modulator of protein phosphatases is an agonist or antagonist of receptors for intercellular messengers which are known to modulate protein phosphatases, said receptors selected from the group consisting of adenosine, adrenoreceptors, angiotensin, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin, vasopressin and oxytocin, VIP, and modulators of calcium or potassium ion channels.

21. A method of treating amyloidosis associated with Alzheimer's disease in a mammalian patient comprising administering to said patient in need of treatment an effective amount of at least one modulator of protein kinase or phosphatase, said modulator capable of controlling the proteolytic processing or function of proteins in mammalian cells.

22. A method according to claim 21 wherein said modulator is a direct or indirect modulator of protein kinase activity.

23. A method according to claim 22 wherein said direct or indirect modulator of protein kinase activity is a selected from the group consisting of phorbol esters, indolactam, mezerin, diacylglycerol, cAMP, cGMP, and their analogs, forskolin, activators or inhibitors of adenylate and guanylate cyclase, activators or inhibitors of phospholipase C, and compounds increasing intracellular calcium.

24. A method according to claim 23 wherein said phorbol ester is selected from the group consisting of phorbol-12,13-dibutyrate, phorbol 12-myristate 13-acetate and their analogs.

25. A method according to claim 23 wherein the indolactam is (-)-7-octylindolactam V.

26. A method according to claim 22 wherein said indirect modulator of protein kinases is an agonist or antagonist of receptors for intercellular messengers which are known to modulate protein kinases said receptors selected from the group consisting of adenosine, adrenoreceptors, angiotensin, atrial natriuretic peptide, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin, vasopressin and oxytocin, VIP, and modulators of calcium or potassium ion channels.

27. A method according to claim 22 wherein said kinase modulator is selected from the group consisting of staurosporine; auranofin; N-(6-aminohexyl)-1-naphthalensulfonamide hydrochloride (W5); N-4(4-aminobutyl)-2-naphthalenesulfonamide hydrochloride (W12); N-(-4-aminobutyl)-5-chloro-2-naphthalenesulfonamide hydrochloride (W13); N-(6-aminohexyl)-5-chloro-1-naphthanesulfamide hydrochloride (W7); 1-(5-isoquinolinesulfonyl)-2-methylpiperazine dihydrochloride (H7); N-(2-(methylamino)ethyl]-3-isoquinolinesulfonamide dihydrochloride (H8); N-(2-aminoethyl)-5-isoquinolinesulfonamide (H9); N(2-guanidinoethyl)-5-isoquinoline-sulfonamide hydrochloride (HA1004); sphingosine and tyrphostin.

28. A method according to claim 22 wherein said modulator is a direct or indirect modulator of protein phosphatase activity.

29. A method according to claim 28 wherein said direct or indirect phosphatase activity is a selected from the group consisting of okadaic acid, calyculin-A, vanadate, and their analogs, FK506, cyclosporin, and compounds increasing intracellular calcium.

30. A method according to claim 28 wherein said indirect modulator of protein phosphatase is an agonist or antagonist of receptors for intercellular messengers which are known to modulate protein phosphatases, said receptors selected from the group consisting of adenosine, adrenoreceptors, angiotensin, bombesin, bradykinin, cholecystokinin and gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin vasopressin and oxytocin, VIP, and modulators of calcium and potassium ion channels.

31. A method according to claim 21 further comprising the administration of at least one agent which affects the endolysomal degradation of APP.

32. The method of claim 31 wherein said agent which affects the endolysomal degradation of APP is chloroquine.

33. A method of screening for an agent that modulates amyloid formation comprising contacting mammalian cells with an agent suspected of being capable of modulating the phosphorylation of proteins and detecting for alterations in the degradation of APP or changes in $\beta/A_4$ peptide production comprising the steps of:
 (a) providing mammalian cells or tissue sections in culture;
 (b) optionally, radioactively labeling proteins produced by the mammalian cells during anabolism; then
 (c) allowing the mammalian cells to continue metabolizing in a suitable, label-free media;
 (d) contacting the mammalian cells at the start of or during step (c) with an agent suspected of being capable of modulating phosphorylation of proteins that occurs during cell metabolism;
 (e) lysing the mammalian cells;
 (f) immunoprecipitating the optionally labeled APP fragments moieties with an antibody against APP; and
 (g) comparing the immunoprecipitated APP or APP fragments to standard APP or APP fragments to detect changes in APP degradation and $\beta/A_4$ peptide production.

34. A method of screening for an agent that modulates amyloid formation comprising administering to a normal or transgenic whole animal an agent suspected of being capable of modulating phosphorylation of proteins and detecting neurodegenerative changes in APP processing, or changes in $\beta/A_4$ peptide production, in the brain of the animal comprising the steps of:
 (a) providing mammalian cells or tissue sections from said animal in culture;
 (b) optionally, radioactively labeling proteins produced by the mammalian cells during anabolism; then
 (c) allowing the mammalian cells to continue metabolizing in a suitable, label-free media;
 (d) contacting the mammalian cells at the start of or during step (c) with an agent suspected of being capable of modulating phosphorylation of proteins that occurs during cell metabolism;
 (e) lysing the mammalian cells;
 (f) immunoprecipitating the optionally labeled APP fragments moieties with an antibody against APP; and
 (g) comparing the immunoprecipitated APP or APP fragments to standard APP or APP fragments to detect changes in APP degradation and $\beta/A_4$ peptide production.

35. The in vitro assay method according to claim 33 wherein the labeling of mammalian cells in step (a) is with [$^{35}$S].

36. The in vitro assay method according to claim 33, wherein the mammalian cells are PC 12 rat pheochromocytoma cells, PC12 cells transfected with the $M_1$ receptor (PC12M$_1$), human umbilical vein endothelial cells (HUVEC), human glioma cells (Hs 683), human neuroblastoma cells (SH SY54), neurons, glia or brain slices.

* * * * *

Adverse Decisions in Interference

Patent No. 5,385,915, Joseph D. Buxbaum, Samuel E. Gandy, Paul Greengard, TREATMENT OF AMYLOIDOSIS ASSOCIATED WITH ALZHEIMER DISEASE USING MODULATORS OF PROTEIN PHOSPHORYLATION, Interference No. 103,915, final judgment adverse to the patentee rendered April 19, 1999, as to claims 33, 35 and 36.

*(Official Gazette June 8, 1999)*